US012661066B2

(12) United States Patent
Hulings et al.

(10) Patent No.: US 12,661,066 B2
(45) Date of Patent: Jun. 23, 2026

(54) ADJUSTABLE MEDICAL GARMENT WITH PRESSURE CONTROL

(71) Applicant: ZOLL Medical Corporation, Chelmsford, MA (US)

(72) Inventors: Robert J. Hulings, Mars, PA (US); Scott D. Quinnell, Kittanning, PA (US); Philip C. Skalos, Pittsburgh, PA (US); Christopher L. Swenglish, Connellsville, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1028 days.

(21) Appl. No.: 17/591,890

(22) Filed: Feb. 3, 2022

(65) Prior Publication Data

US 2022/0249024 A1 Aug. 11, 2022

Related U.S. Application Data

(60) Provisional application No. 63/146,019, filed on Feb. 5, 2021.

(51) Int. Cl.
A61B 5/00 (2006.01)
A61B 5/05 (2021.01)
(Continued)

(52) U.S. Cl.
CPC .............. A61B 5/6843 (2013.01); A61B 5/05 (2013.01); A61B 5/1102 (2013.01); A61B 5/256 (2021.01);
(Continued)

(58) Field of Classification Search
CPC ....... A61B 5/6843; A61B 5/05; A61B 5/1102; A61B 5/256; A61B 5/282; A61B 5/6805;
(Continued)

(56) References Cited

U.S. PATENT DOCUMENTS

| | | |
|---|---|---|
| 4,928,690 A | 5/1990 | Heilman et al. |
| 5,741,306 A | 4/1998 | Glegyak |

(Continued)

OTHER PUBLICATIONS

TactilusÅ® real-time surface pressure mapping technology. Tactile Surface Sensor | Real-time Surface Pressure Mapping Technology | Pressure Pad | Force Sensitive Resistor | Matrix Tactile Sensor | Pressure Mapping System FSR. (2013). tactilus.net/ (Year: 2013).*

(Continued)

*Primary Examiner* — Jennifer Robertson
*Assistant Examiner* — Elina Sohyun Jang
(74) *Attorney, Agent, or Firm* — Secant IP, P.L.L.C.

(57) ABSTRACT

A wearable cardiac monitoring device for providing an improved fit to a body of a patient during long term cardiac monitoring of the patient is provided. The device includes a garment configured to be worn about a torso of the patient and including a flexible material and physiological sensors configured to detect a physiological signal of the patient, the physiological sensors disposed on the flexible material and positioned at one or more anatomical locations of the patient's torso. The device also includes force applicators disposed on the flexible material proximate to the one or more physiological sensors, each of the force applicators configured to be adjustable during the long term cardiac monitoring of the patient to cause a pressure in a range of 0.05 psi to 0.65 psi to be exerted by the physiological sensors onto the one or more anatomical locations of the patient's torso.

27 Claims, 25 Drawing Sheets

(51) Int. Cl.

| | |
|---|---|
| *A61B 5/11* | (2006.01) |
| *A61B 5/256* | (2021.01) |
| *A61B 5/282* | (2021.01) |
| *A61N 1/04* | (2006.01) |
| *A61N 1/39* | (2006.01) |

(52) U.S. Cl.
CPC ............ *A61B 5/282* (2021.01); *A61B 5/6805* (2013.01); *A61N 1/3925* (2013.01); *A61B 2562/0209* (2013.01); *A61N 1/046* (2013.01); *A61N 1/0476* (2013.01); *A61N 1/0484* (2013.01)

(58) Field of Classification Search
CPC ............ A61B 2562/0209; A61B 5/259; A61B 5/0006; A61B 5/0022; A61B 5/318; A61B 5/335; A61B 5/6823; A61B 2562/08; A61B 5/002; A61B 5/0205; A61B 5/026; A61B 5/0295; A61B 5/0537; A61B 5/11; A61B 5/1112; A61B 5/1113; A61B 5/1114; A61B 5/1116; A61B 5/1117; A61B 5/1118; A61B 5/14532; A61B 5/33; A61B 5/369; A61B 5/389; A61B 5/4076; A61B 5/411; A61B 5/4803; A61B 5/4806; A61B 5/681; A61B 5/6816; A61B 5/6822; A61B 5/6826; A61B 5/6838; A61B 5/6898; A61B 5/7203; A61B 5/7225; A61B 5/7267; A61B 5/7271; A61B 5/7435; A61B 5/7455; A61B 5/7465; A61B 5/7475; A61B 8/565; A61B 5/0008; A61B 5/02055; A61B 5/02438; A61B 5/1038; A61B 5/112; A61B 5/1124; A61B 5/1128; A61B 5/1176; A61B 5/224; A61B 5/4023; A61B 5/4519; A61B 5/4528; A61B 5/7214; A61B 5/726; A61B 5/743; A61B 8/0808; A61B 8/56; A61B 2505/01; A61B 2560/0214; A61B 2560/0223; A61B 2560/0468; A61B 2562/0219; A61B 5/30; A61N 1/3925; A61N 1/046; A61N 1/0476; A61N 1/0484; A61N 1/36507; A61N 1/3904; G16H 40/63; G16H 40/67; G16H 50/20; G16H 10/60; G16H 20/60; G16H 30/20
See application file for complete search history.

(56) References Cited

U.S. PATENT DOCUMENTS

| | | | |
|---|---|---|---|
| 5,929,601 | A | 7/1999 | Kaib et al. |
| 5,944,669 | A | 8/1999 | Kaib |
| 6,065,154 | A | 5/2000 | Hulings |
| 6,097,982 | A | 8/2000 | Glegyak |
| 6,253,099 | B1 | 6/2001 | Oskin |
| 6,681,003 | B2 | 1/2004 | Linder |
| 9,833,607 | B2 | 12/2017 | Crone et al. |
| 9,987,496 | B2 | 6/2018 | Sullivan |
| 2008/0065042 | A1 | 3/2008 | Wood et al. |
| 2012/0158074 | A1 | 6/2012 | Hall |
| 2012/0220192 | A1 | 8/2012 | Swendseid |
| 2014/0093853 | A1* | 4/2014 | Constantine, III ... G09B 23/288 |
| | | | 434/265 |
| 2014/0331380 | A1 | 11/2014 | Brown |
| 2015/0031964 | A1* | 1/2015 | Bly ........................ A61B 5/681 |
| | | | 600/300 |
| 2016/0021943 | A1 | 1/2016 | Das |
| 2017/0027235 | A1 | 2/2017 | Inzer |
| 2017/0027252 | A1 | 2/2017 | Inzer |
| 2017/0100300 | A1* | 4/2017 | Rapp ...................... A61F 13/10 |
| 2017/0273365 | A1 | 9/2017 | Muhlenfeld |
| 2018/0003579 | A1* | 1/2018 | Esposito ................... A41F 9/00 |
| 2018/0221648 | A1 | 8/2018 | Gustavson |
| 2018/0243549 | A1 | 8/2018 | Hill et al. |
| 2019/0082800 | A1* | 3/2019 | Baranski .............. A44C 5/2071 |
| 2019/0298987 | A1 | 10/2019 | Freeman |
| 2020/0037673 | A1 | 2/2020 | Storelli |
| 2020/0155861 | A1 | 5/2020 | Chapman et al. |
| 2021/0076971 | A1* | 3/2021 | Oloumi ............... A61B 5/0205 |
| 2022/0095946 | A1* | 3/2022 | Ji ........................... A61B 5/742 |
| 2024/0090775 | A1* | 3/2024 | Gargiulo ............. H10N 30/302 |

OTHER PUBLICATIONS

Bluestein et al., Pressure Ulcers: Prevention, Evaluation and Management, American Family Physician www.aafp.org/afp., vol. 78, No. 10 (pp. 1186-1194) Nov. 15, 2008 (9 pages).
Dharmarajan et al., Pressure Ulcers: Clinical Features and Management, Hospital Physician www.turner-white.com (pp. 64-71) Mar. 2002 (8 pages).
Grey et al., ABC of Wound Healing—Pressure Ulcers, BMJ, vol. 332 (pp. 472-475) Feb. 25, 2006 (4 pages).
Grada et al., Pressure Ulcers—Dermatologic Disorders—Merck Manuals Professional Edition, https://www.merckmanuals.com/professional/dermatologic-disorders/pressure-ulcers/pressure-ulcers#, Downloaded Feb. 18, 2020 (11 pages).

* cited by examiner

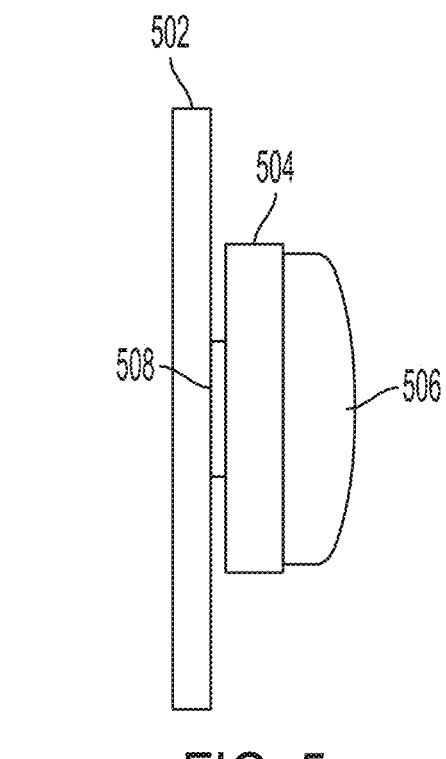
FIG. 5
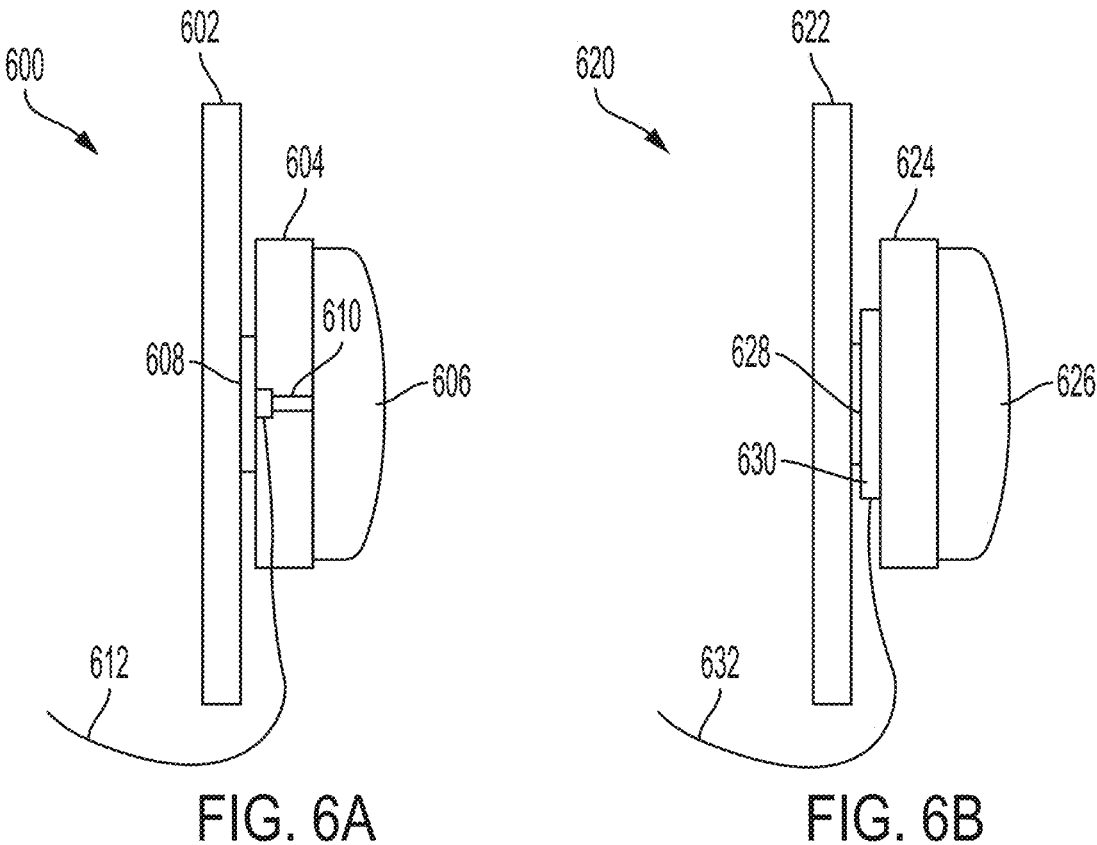
FIG. 6A           FIG. 6B

900

1050

1052

1800

1810

ADJUSTABLE MEDICAL GARMENT WITH PRESSURE CONTROL

RELATED APPLICATION

This application claims priority under 35 U.S.C. § 119 (e) to U.S. Provisional Application Ser. No. 63/146,019, titled "ADJUSTABLE MEDICAL GARMENT WITH PRESSURE CONTROL," filed Feb. 5, 2021, which is hereby incorporated herein by reference in its entirety.

BACKGROUND

The present disclosure is directed to a medical garment for a variety of monitoring, diagnostic, and treatment purposes that is adjustable to be physically comfortable to the patient through pressure control methods and systems.

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient wears the device during all daily activities such as walking, sitting, climbing stairs, resting or sleeping, and other similar daily activities. Maintaining continuous or near-continuous use of the device as pre-scribed can be important for monitoring patient progress as well as providing treatment to the patient if needed.

SUMMARY

In at least one example, a wearable cardiac monitoring device for providing an improved fit to a body of a patient during long term cardiac monitoring of the patient is provided. The device includes a garment configured to be worn about a torso of the patient and including a flexible material, one or more physiological sensors and associated circuitry configured to detect a physiological signal of the patient, the one or more physiological sensors disposed on the flexible material and positioned at one or more anatomical locations of the patient's torso, and one or more force applicators disposed on the flexible material proximate to the one or more physiological sensors, each of the one or more force applicators configured to be adjustable during the long term cardiac monitoring of the patient to cause a pressure in a range of 0.05 psi to 0.65 psi to be exerted by the one or more physiological sensors onto the one or more anatomical locations of the patient's torso.

Implementation of the wearable cardiac monitoring device can include one or more of the following features.

In examples of the wearable cardiac monitoring device, the one or more force applicators are further configured to adjust the pressure to a range between 0.65 psi to 5.0 psi during a high-force event. In some examples, the one or more force applicators are further configured to adjust the pressure to the range between 0.05 psi and 0.65 psi after the high-force event. In some examples, the high-force event includes at least one of delivery of at least one treatment pulse, a radio-frequency (RF) monitoring period, a monitoring period during high noise detection, and a monitoring period including a falloff event. In some examples, the high-force event spans a predetermined brief period of time. In some examples, the predetermined brief period of time includes at least one of 5 seconds, 10 seconds, 15 seconds, 20 seconds, 25 seconds, 30 seconds, 45 seconds, and 60 seconds.

In examples of the wearable cardiac monitoring device, the pressure range of 0.05 psi to 0.65 psi is determined by an external pressure measurement device configured to measure an average pressure exerted by the one or more physiological sensors on the one or more anatomical locations of the patient's torso. In some examples, the external pressure measurement device includes a mannequin structure for wearably mounting the garment and a plurality of pressure sensors distributed at a plurality of locations on the mannequin structure corresponding to the one or more anatomical locations of the patient's torso.

In examples of the wearable cardiac monitoring device, the one or more force applicators are calibrated to cause the pressure range of 0.05 psi to 0.65 psi to be exerted based on an external measurement device configured to measure the pressure exerted by the one or more physiological sensors on the one or more anatomical locations of the patient's torso. In some examples, the external pressure measurement device includes a mannequin structure for wearably mounting the garment and a plurality of pressure sensors distributed at a plurality of locations on the mannequin structure corresponding to the one or more anatomical locations of the patient's torso.

In examples of the wearable cardiac monitoring device, the cardiac monitoring device can further include a controller operably connected to the one or more force applicators and configured to control the one or more force applicators to adjust the pressure exerted by the one or more physiological sensors during the long term cardiac monitoring of the patient.

In examples of the wearable cardiac monitoring device, the long term cardiac monitoring of the patient includes continuous, long term monitoring of the patient.

In examples of the wearable cardiac monitoring device, the one or more physiological sensors and associated circuitry include one or more electrocardiogram (ECG) sensors and associated circuitry configured to detect a cardiac signal of the patient. In some examples, the one or more ECG sensors are disposed between the one or more force applicators and the one or more anatomical locations such that the one or more force applicators are configured to cause the pressure in the range of 0.05 psi to 0.65 psi to be exerted on the one or more ECG sensors during monitoring of the cardiac signal.

In examples of the wearable cardiac monitoring device, the one or more physiological sensors and associated circuitry include one or more therapy electrodes configured to deliver one or more therapeutic shocks to the patient. In some examples, the one or more therapy electrodes are disposed between the one or more force applicators and the one or more anatomical locations such that the one or more force applicators are configured to cause the pressure in the range of 0.05 psi to 0.65 psi to be exerted on the one or more therapy electrodes during delivery of the one or more therapeutic shocks to the patient.

In examples of the wearable cardiac monitoring device, the one or more physiological sensors and associated circuitry include an RF ultra-wide band transceiver circuit including one or more RF antennas and are configured to generate one or more RF-based measurements.

In some examples, the RF ultra-wide band transceiver circuit is configured to generate one or more RF-based measurements by being configured to control the one or more RF antennas to direct RF electromagnetic energy into a thoracic cavity of the patient and derive RF information responsive to reflected RF electromagnetic energy received through the one or more RF antennas and reflected from within the thoracic cavity of the patient. In some examples, the one or more RF-based measurements include one or more of an arterial pulse measurement of the patient, a thoracic lung fluid measurement of the patient, and a heart wall movement measurement of the patient. In some examples, the RF ultra-wide band transceiver circuit is disposed between the one or more force applicators and the one or more anatomical locations such that the one or more force applicators are configured to cause the pressure in the range of 0.05 psi to 0.65 psi to be exerted on the RF ultra-wide band transceiver circuit during generation of the one or more RF-based measurements.

In examples of the wearable cardiac monitoring device, the one or more physiological sensors and associated circuitry include one or more vibrational sensors configured to detect one or more cardio-vibrational signals of the patient. In some examples, the one or more vibrational sensors are disposed between the one or more force applicators and the one or more anatomical locations such that the one or more force applicators are configured to cause the pressure in the range of 0.05 psi to 0.65 psi to be exerted on the vibrational sensor during detection of the one or more cardio-vibrational signals of the patient.

In examples of the wearable cardiac monitoring device, the wearable cardiac monitoring device can further include one or more sensor attachments disposed on the flexible material to receive and position the one or more physiological sensors at the one or more anatomical locations of the patient's torso. In some examples, the one or more sensor attachments include one or more of a mechanical fastener, an enclosed receptacle, and an adhesive fastener. In some examples, the one or more sensor attachments are disposed on the garment such that the one or more physiological sensors align with one or more anatomical locations of the patient's torso when the garment is worn by the patient. In some examples, the one or more force applicators are configured to be removably coupled to at least one of the one or more sensor attachments and disposed within at least a portion of the garment corresponding to at least one of the one or more sensor attachments.

In examples of the wearable cardiac monitoring device, the one or more anatomical locations of the patient's torso include locations on the torso of the patient where the one or more physiological sensors are to be positioned during the long term monitoring of the patient.

In examples of the wearable cardiac monitoring device, the one or more force applicators include one or more electro-mechanical force applicators, one or more mechanical force applicators, and one or more fluid reservoir-based force applicators.

In examples of the wearable cardiac monitoring device, the one or more force applicators are integrated into the one or more physiological sensors and associated circuitry.

In examples of the wearable cardiac monitoring device, the one or more force applicators are integrated into the garment.

In examples of the wearable cardiac monitoring device, the wearable cardiac monitoring device can further include one or more pressure sensors disposed proximate to the one or more force applicators and configured to measure the pressure exerted between the one or more physiological sensors and the one or more anatomical locations of the patient's torso to produce at least one measured pressure. In some examples, the one or more pressure sensors include at least one visual indicator configured to provide an indication of the at least one measured pressure. In some examples, the one or more pressure sensors are configured to operatively communicate with a remote computing device. In some examples, the remote computing device is configured to receive one or more pressure signals from the one or more pressure sensors and provide an indication of the at least one measured pressure.

In examples of the wearable cardiac monitoring device, the one or more force applicators are further configured to cause a pressure in the range of 0.05 psi to 0.62 psi to be exerted from the one or more physiological sensors on to the one or more anatomical locations of the patient's torso.

In examples of the wearable cardiac monitoring device, the patient is prescribed the wearable cardiac monitoring device for a prescribed period of time during which the device provides the long term cardiac monitoring of the patient, the prescribed period of time including at least one of at least three days, between three days and one week, between one week and two weeks, between two weeks and one month, between one month and three months, between three months and six months, and more than six months.

In another example, a wearable cardiac monitoring device and garment for providing an improved fit to a body of a patient during long term cardiac monitoring of the patient is provided. The wearable cardiac monitoring device and garment includes a garment configured to be worn about a torso of the patient and including a flexible material, one or more physiological sensors and associated circuitry configured to detect a physiological signal of the patient, the one or more physiological sensors disposed on the flexible material and positioned at one or more anatomical locations of the patient's torso, and one or more force applicators disposed on the flexible material proximate to the one or more physiological sensors, each of the one or more force applicators configured to be adjustable during the long term cardiac monitoring of the patient to cause a pressure in a range of 0.05 psi to 0.65 psi to be exerted by the one or more physiological sensors onto the one or more anatomical locations of the patient's torso, and at least one controller operably coupled to the one or more force applicators. The at least one controller is configured to monitor a respective pressure between each of the one or more physiological sensors and a corresponding anatomical location of the patient's torso, and if the respective pressure at a monitored physiological sensor is out of the range of 0.05 psi to 0.65 psi, adjust the pressure at a corresponding force applicator such that the respective pressure between the monitored physiological sensor and a corresponding anatomical location of the patient's torso is in a range of 0.05 psi to 0.65 psi.

Implementations of the wearable cardiac monitoring device and garment can include one or more of the following features.

In examples of the wearable cardiac monitoring device and garment, the one or more force applicators are further configured to adjust the pressure to a range between 0.65 psi to 5.0 psi during a high-force event. In some examples, the one or more force applicators are further configured to adjust the pressure to the range between 0.05 psi and 0.65 psi after the high-force event. In some examples, the high-force event includes at least one of delivery of at least one treatment pulse, an RF monitoring period, a monitoring period during high noise detection, and a monitoring period including a falloff event. In some examples, the high-force event spans a predetermined brief period of time. In some examples, the predetermined brief period of time includes at least one of 5 seconds, 10 seconds, 15 seconds, 20 seconds, 25 seconds, 30 seconds, 45 seconds, and 60 seconds.

In examples of the wearable cardiac monitoring device and garment, the pressure range of 0.05 psi to 0.65 psi is determined by an external pressure measurement device configured to measure an average pressure exerted by the one or more physiological sensors on the one or more anatomical locations of the patient's torso. In some examples, the external pressure measurement device includes a mannequin structure for wearably mounting the garment and a plurality of pressure sensors distributed at a plurality of locations on the mannequin structure corresponding to the one or more anatomical locations of the patient's torso.

In examples of the wearable cardiac monitoring device and garment, the one or more force applicators are calibrated to cause the pressure range of 0.05 psi to 0.65 psi to be exerted based on an external measurement device configured to measure the pressure exerted by the one or more physiological sensors on the one or more anatomical locations of the patient's torso. In some examples, the external pressure measurement device includes a mannequin structure for wearably mounting the garment and a plurality of pressure sensors distributed at a plurality of locations on the mannequin structure corresponding to the one or more anatomical locations of the patient's torso.

In examples of the wearable cardiac monitoring device and garment, the long term cardiac monitoring of the patient includes continuous, long term monitoring of the patient.

In examples of the wearable cardiac monitoring device and garment, the wearable cardiac monitoring device and garment can further include one or more pressure sensors disposed proximate to the one or more force applicators and configured to measure the pressure exerted between the one or more physiological sensors and the one or more anatomical locations of the patient's torso. In some examples, the one or more pressure sensors are configured to operatively communicate with the at least one controller. In some examples, the at least one controller is configured to monitor a respective pressure by being configured to receive one or more pressure signals from the one or more pressure sensors and determine the respective pressure between each of the one or more physiological sensors and a corresponding anatomical location of the patient's torso.

In examples of the wearable cardiac monitoring device and garment, the one or more physiological sensors and associated circuitry include one or more ECG sensors and associated circuitry configured to detect a cardiac signal of the patient. In some examples, the one or more ECG sensors are disposed between the one or more force applicators and the one or more anatomical locations such that the one or more force applicators are configured to cause the pressure in the range of 0.05 psi to 0.65 psi to be exerted on the one or more ECG sensors during monitoring of the cardiac signal.

In examples of the wearable cardiac monitoring device and garment, the one or more physiological sensors and associated circuitry include one or more therapy electrodes configured to deliver one or more therapeutic shocks to the patient. In some examples, the one or more therapy electrodes are disposed between the one or more force applicators and the one or more anatomical locations such that the one or more force applicators are configured to cause the pressure in the range of 0.05 psi to 0.65 psi to be exerted on the one or more therapy electrodes during delivery of the one or more therapeutic shocks to the patient.

In examples of the wearable cardiac monitoring device and garment, the one or more physiological sensors and associated circuitry include an RF ultra-wide band transceiver circuit including one or more RF antennas and are configured to generate one or more RF-based measurements. In some examples, the RF ultra-wide band transceiver circuit is configured to generate one or more RF-based measurements by being configured to control the one or more RF antennas to direct RF electromagnetic energy into a thoracic cavity of the patient and derive RF information responsive to reflected RF electromagnetic energy received through the one or more RF antennas and reflected from within the thoracic cavity of the patient. In some examples, the one or more RF-based measurements include one or more of an arterial pulse measurement of the patient, a thoracic lung fluid measurement of the patient, and a heart wall movement measurement of the patient. In some examples, the RF ultra-wide band transceiver circuit is disposed between the one or more force applicators and the one or more anatomical locations such that the one or more force applicators are configured to cause the pressure in the range of 0.05 psi to 0.65 psi to be exerted on the RF ultra-wide band transceiver circuit during generation of the one or more RF-based measurements.

In examples of the wearable cardiac monitoring device and garment, the one or more physiological sensors and associated circuitry include one or more vibrational sensors configured to detect one or more cardio-vibrational signals of the patient. In some examples, the one or more vibrational sensors are disposed between the one or more force applicators and the one or more anatomical locations such that the one or more force applicators are configured to cause the pressure in the range of 0.05 psi to 0.65 psi to be exerted on the vibrational sensor during detection of the one or more cardio-vibrational signals of the patient.

In examples of the wearable cardiac monitoring device and garment, the wearable cardiac monitoring device and garment can further includes one or more sensor attachments disposed on the flexible material to receive and position the one or more physiological sensors at the one or more anatomical locations of the patient's torso. In some examples, the one or more sensor attachments include one or more of a mechanical fastener, an enclosed receptacle, and an adhesive fastener. In some examples, the one or more sensor attachments are disposed on the garment such that the one or more physiological sensors align with one or more anatomical locations of the patient's torso when the garment is worn by the patient. In some examples, the one or more force applicators are configured to be removably coupled to at least one of the one or more sensor attachments and disposed within at least a portion of the garment corresponding to at least one of the one or more sensor attachments.

In examples of the wearable cardiac monitoring device and garment, the one or more force applicators include one or more electro-mechanical force applicators, one or more mechanical force applicators, and one or more fluid reservoir-based force applicators.

In examples of the wearable cardiac monitoring device and garment, the one or more force applicators are integrated into the one or more physiological sensors and associated circuitry.

In examples of the wearable cardiac monitoring device and garment, the one or more force applicators are integrated into the garment.

In another example, a second wearable cardiac monitoring device and garment for providing an improved fit to a body of a patient during long term cardiac monitoring of the patient is provided. The device includes one or more physiological sensors and associated circuitry configured to detect a physiological signal of the patient, a garment configured to be worn about a torso of the patient, the garment including a flexible material, wherein the one or more physiological sensors are disposed on the flexible material and configured to be positioned at one or more anatomical locations of the patient's torso, and one or more force applicators disposed proximate to the one or more physiological sensors, each of the one or more force applicators being configured to exert a force on at least one of the one or more physiological sensors and including a user-adjustable interface and at least one mechanical force adjuster configured to alter the exerted force in response to manipulation of the user-adjustable interface to cause a pressure in a range of 0.05 psi to 0.65 psi to be exerted from the one or more physiological sensors on to the one or more anatomical locations of the patient's torso during the long term cardiac monitoring of the patient.

Implementations of the second wearable cardiac monitoring device and garment can include one or more of the following features.

In examples of the second wearable cardiac monitoring device and garment, the user-adjustable interface includes a mechanical interface configured to be manipulated by a user to alter the exerted force. In some examples, the mechanical interface includes at least one of a toolless mechanical interface and a mechanical interface configured to be manipulated by a tool.

In examples of the second wearable cardiac monitoring device and garment, the user-adjustable interface includes a receptacle configured to receive at least one of a shim and a spacer to alter the exerted force.

In examples of the second wearable cardiac monitoring device and garment, the one or more physiological sensors and associated circuitry include one or more ECG sensors and associated circuitry configured to detect a cardiac signal of the patient. In some examples, the one or more ECG sensors are disposed between the one or more force applicators and the one or more anatomical locations such that the one or more force applicators are configured to cause the pressure in the range of 0.05 psi to 0.65 psi to be exerted on the one or more ECG sensors during monitoring of the cardiac signal.

In examples of the second wearable cardiac monitoring device and garment, the one or more physiological sensors and associated circuitry include one or more therapy electrodes configured to deliver one or more therapeutic shocks to the patient. In some examples, the one or more therapy electrodes are disposed between the one or more force applicators and the one or more anatomical locations such that the one or more force applicators are configured to cause the pressure in the range of 0.05 psi to 0.65 psi to be exerted on the one or more therapy electrodes during delivery of the one or more therapeutic shocks to the patient.

In examples of the second wearable cardiac monitoring device and garment, the one or more physiological sensors and associated circuitry include an RF ultra-wide band transceiver circuit including one or more RF antennas and are configured to generate one or more RF-based measurements. In some examples, the RF ultra-wide band transceiver circuit is configured to generate one or more RF-based measurements by being configured to control the one or more RF antennas to direct RF electromagnetic energy into a thoracic cavity of the patient and derive RF information responsive to reflected RF electromagnetic energy received through the one or more RF antennas and reflected from within the thoracic cavity of the patient. In some examples, the one or more RF-based measurements include one or more of an arterial pulse measurement of the patient, a thoracic lung fluid measurement of the patient, and a heart wall movement measurement of the patient. In some examples, the RF ultra-wide band transceiver circuit is disposed between the one or more force applicators and the one or more anatomical locations such that the one or more force applicators are configured to cause the pressure in the range of 0.05 psi to 0.65 psi to be exerted on the RF ultra-wide band transceiver circuit during generation of the one or more RF-based measurements.

In examples of the second wearable cardiac monitoring device and garment, the one or more physiological sensors and associated circuitry include one or more vibrational sensors configured to detect one or more cardio-vibrational signals of the patient. In some examples, the one or more vibrational sensors are disposed between the one or more force applicators and the one or more anatomical locations such that the one or more force applicators are configured to cause the pressure in the range of 0.05 psi to 0.65 psi to be exerted on the vibrational sensor during detection of the one or more cardio-vibrational signals of the patient.

In examples of the second wearable cardiac monitoring device and garment, the second wearable cardiac monitoring device and garment can further include one or more sensor attachments disposed on the flexible material to receive and position the one or more physiological sensors at the one or more anatomical locations of the patient's torso. In some examples, the one or more sensor attachments include one or more of a mechanical fastener, an enclosed receptacle, and an adhesive fastener. In some examples, the one or more sensor attachments are disposed on the garment such that the one or more physiological sensors align with one or more anatomical locations of the patient's torso when the garment is worn by the patient. In some examples, the one or more force applicators are configured to be removably coupled to at least one of the one or more sensor attachments and disposed within at least a portion of the garment corresponding to at least one of the one or more sensor attachments.

In examples of the second wearable cardiac monitoring device and garment, the one or more force applicators are integrated into the one or more physiological sensors and associated circuitry.

In examples of the second wearable cardiac monitoring device and garment, the one or more force applicators are integrated into the garment.

In examples of the second wearable cardiac monitoring device and garment, the long term cardiac monitoring of the patient includes continuous, long term monitoring of the patient.

In another example, a system for monitoring and providing feedback regarding pressure applied to a body of a patient during long term cardiac monitoring of the patient is provided. The system includes at least one pressure sensor configured to monitor at least one pressure between one or more physiological sensors at one or more anatomical locations of a patient's torso and at least one processor operably coupled to the at least one pressure sensor. The at least one processor is configured to receive at least one sensor signal from the at least one pressure sensor, identify at least one location on the body of the patient that is associated with the at least one pressure sensor, derive, based upon the at least one sensor signal, the least one derived exerted pressure exerted from the one or more physiological sensors on to the one or more anatomical locations of the patient's torso, determine at least one measurement of the at least one derived exerted pressure, and where the least one measurement is outside of a range of 0.05 psi to 0.65 psi, provide an alert including the at least one location on the patient's body and one or more of the measurement and an indication whether the at least one derived exerted pressure is to be increased or decreased.

Implementations of the system for monitoring and providing feedback regarding pressure applied to a body of a patient during long term cardiac monitoring of the patient can include one or more of the following features.

In examples of the system, the at least one processor is integrated into at least one of the one or more physiological sensors.

In examples of the system, the at least one processor is integrated into a remote computing device operably coupled to and in communication with the at least one pressure sensor.

In examples of the system, the one or more physiological sensors include one or more ECG sensors and associated circuitry configured to detect a cardiac signal of the patient. In some examples, the one or more ECG sensors are disposed between one or more force applicators and the one or more anatomical locations such that the one or more force applicators are configured to cause the pressure in the range of 0.05 psi to 0.65 psi to be exerted on the one or more ECG sensors during monitoring of the cardiac signal.

In examples of the system, the one or more physiological sensors include one or more therapy electrodes configured to deliver one or more therapeutic shocks to the patient. In some examples, the one or more therapy electrodes are disposed between one or more force applicators and the one or more anatomical locations such that the one or more force applicators are configured to cause the pressure in the range of 0.05 psi to 0.65 psi to be exerted on the one or more therapy electrodes during delivery of the one or more therapeutic shocks to the patient.

In examples of the system, the one or more physiological include an RF ultra-wide band transceiver circuit including one or more RF antennas and are configured to generate one or more RF-based measurements. In some examples, the RF ultra-wide band transceiver circuit is configured to generate one or more RF-based measurements by being configured to control the one or more RF antennas to direct RF electromagnetic energy into a thoracic cavity of the patient and derive RF information responsive to reflected RF electromagnetic energy received through the one or more RF antennas and reflected from within the thoracic cavity of the patient. In some examples, the one or more RF-based measurements include one or more of an arterial pulse measurement of the patient, a thoracic lung fluid measurement of the patient, and a heart wall movement measurement of the patient. In some examples, the RF ultra-wide band transceiver circuit is disposed between one or more force applicators and the one or more anatomical locations such that the one or more force applicators are configured to cause the pressure in the range of 0.05 psi to 0.65 psi to be exerted on the RF ultra-wide band transceiver circuit during generation of the one or more RF-based measurements.

In examples of the system, the one or more physiological sensors include one or more vibrational sensors configured to detect one or more cardio-vibrational signals of the patient. In some examples, the one or more vibrational sensors are disposed between one or more force applicators and the one or more anatomical locations such that the one or more force applicators are configured to cause the pressure in the range of 0.05 psi to 0.65 psi to be exerted on the vibrational sensor during detection of the one or more cardio-vibrational signals of the patient.

In examples of the system, the long term cardiac monitoring of the patient includes continuous, long term monitoring of the patient.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 5 illustrates an alternative arrangement of a force applicator positioned between a garment and a sensor, in accordance with an example of the present disclosure.

FIGS. 6A and 6B illustrate a sample arrangement of a force applicator and a sensor further including a pressure sensor, in accordance with an example of the present disclosure.

DETAILED DESCRIPTION

Figure 1:
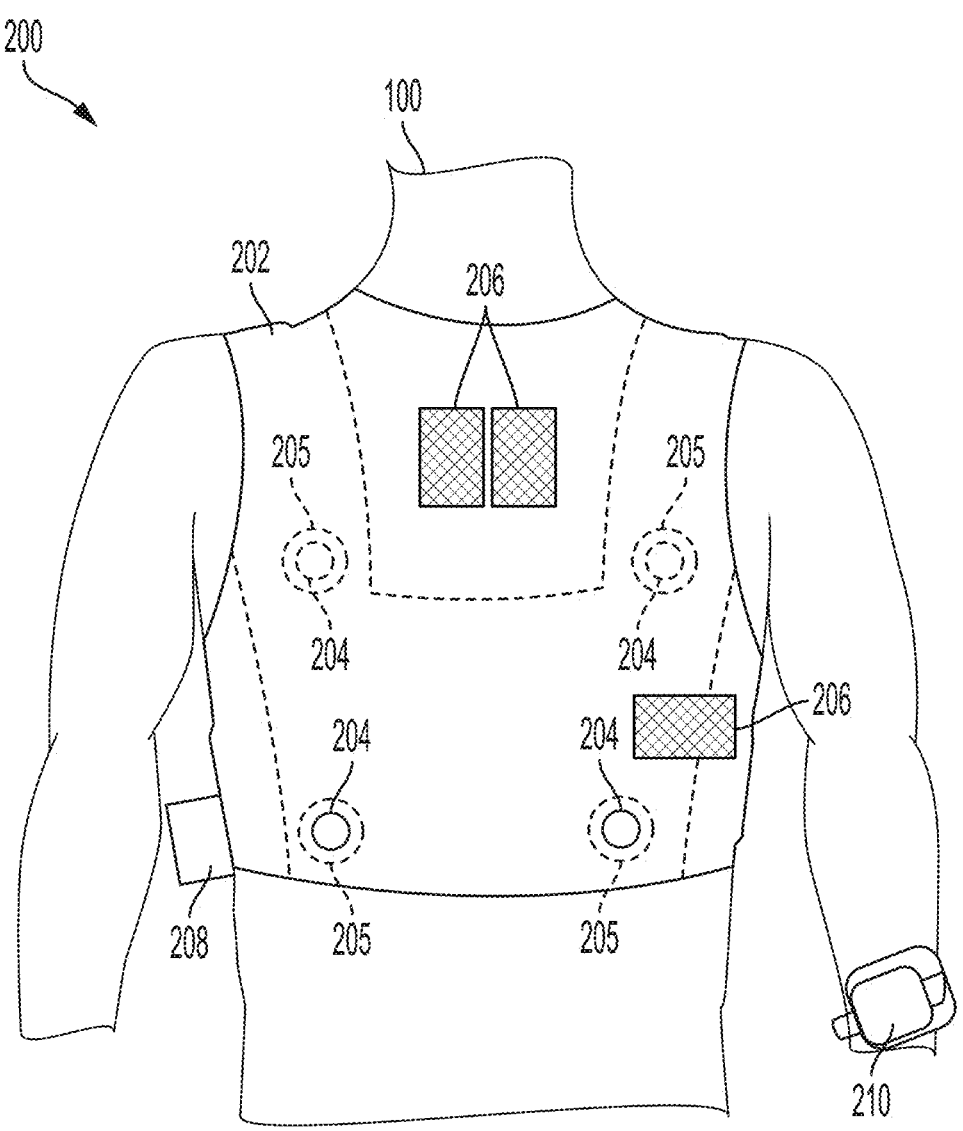
FIG. 1 illustrates a sample garment with a first arrangement of sensors, in accordance with an example of the present disclosure.

As summarized above, some examples disclosed herein are directed to a medical garment that dynamically adjusts to maintain a proper fit between a wearable medical device and a patient. Examples of wearable medical devices that can benefit from incorporating such a garment include cardiac event monitoring and/or treatment devices. These wearable medical devices are used in clinical or outpatient settings to monitor and/or record various electrocardiogram (ECG) and other physiological signals of a patient. Moreover, these wearable medical devices can analyze the ECG and other physiological signals to monitor for arrhythmias, and, in example devices described herein, provide treatment such as cardioverting, defibrillating, or pacing shocks in the event of life-threatening arrhythmias. Examples of cardiac monitoring and treatment devices that can implement the adjustable garment features and/or processes described herein includes mobile cardiac telemetry (MCT) devices; wearable defibrillators, which are also called wearable cardioverter defibrillator (WCDs); and hospital wearable defibrillators (HWDs), to name but a few.

To effectively monitor and, if needed, provide treatment to a patient, the patient should wear the device as close to continuously as possible. To such an end, providing patient comfort while still having a garment that is tight enough to provide good sensor-skin interfaces, e.g., secure contact between a physiological sensor and the patient's skin, is important to overall medical device efficiency and effectiveness. By improving the comfort for the patient, while still maintaining high levels of monitoring quality, the patient is more likely to continue wearing the device during a prescribed period, which increases the overall effectiveness of the wearable medical device, increases quality of the data collected by the wearable medical device for analysis by the patient's physician, and increases the likelihood that treatment, if necessary, will be properly delivered to the patient when needed as the patient is continuously and properly wearing the medical device as prescribed.

For example, a processor in the wearable medical device can be configured to monitor for pressure values at one or more sensor-skin interfaces as described herein. The processor can compare the monitored pressure values to determine if they are within an acceptable range. For example, an acceptable pressure range can include pressures between 0.25 psi and 0.62 psi. If the pressure at a sensor-skin interface is outside of the acceptable range, the processor can issue a notification that the pressure is outside the range and/or automatically adjust a force applicator associated with the sensor-skin interface to adjust its exerted force on the physiological sensor at that interface, thereby adjusting the resulting pressure.

The acceptable pressure range can be selected based upon a minimum pressure that provides adequate contact between a physiological sensor and the patient's skin and a maximum pressure that, above which, may cause the patient discomfort such as the development of pressure ulcers. As such, the systems and methods as described herein can be used to provide added comfort to the patient by reducing the risk that they will suffer pressure ulcers or other similar negative side effects of long-term wear of a wearable medical device while maintaining a high level of device efficiency resulting from quality sensor contact at each sensor-skin interface.

As described herein, a wearable medical device can be configured to exert a pressure between a physiological sensor and the patient's skin in a comfortable pressure range of 0.05 psi to 0.65 psi for an extended period of time. It should be noted that, based upon patient activity such as sitting, standing, walking, bending over, and other similar movements, an instantaneous pressure at one or more of the physiological sensors as exerted on the patient's skin can exceed the comfortable pressure range. However, as described herein, the comfortable pressure range can represent an average exerted pressure over the extended period of wear of the medical device. As such, the wearable medical device as described herein can be configured to provide an average exerted pressure between physiological sensors and the patient's skin in a comfortable pressure range of 0.05 psi to 0.65 psi over the entire extended period of wear.

In some examples, the comfortable patient pressure range of 0.05 psi to 0.65 psi may be exceeded briefly in certain circumstances, such as when the wearable medical device is performing certain critical functions. The clinical and animal research supporting the ranges below is as follows. According to a study by Grada and Phillips (*The Merck Manual on Pressure Ulcers,* 2019), applying external pressure to the skin beyond the normal skin capillary pressure range of 12 to 32 mm Hg (0.23 psi to 0.62 psi) reduces oxygen circulation and negatively affects skin tissue. For example, if external skin pressure exceeds 33 mm Hg (0.64 psi), blood vessels can become blocked and tissues becomes anoxic (as cited by a study conducted by Agrawal & Chauhan (*Pressure Ulcers: Back to the Basics,* 2012)). If this pressure is prolonged, " . . . cell death will occur, resulting in soft tissue necrosis and eventual ulceration", or what is commonly described as bedsores or pressure ulcers (Agrawal & Chauhan, 23). How long until discomfort or tissue damage occurs varies, but according to the study by Grada and Phillips, tissue damage appears in as little as 3 to 4 hours when external pressure exceeds 32 mm Hg (0.62 psi). Evidence of skin damage is further supported by a study conducted by Salcido et al. (*An Animal Model and*

*Computer-Controller Surface Pressure Delivery System for the Production of Pressure Ulcers,* 1995) who found that in a study of rats, applying an external force of 35-40 mm Hg (0.68-0.77 psi) for five minute durations resulted in a near zero blood flow, with a complete cutoff at 80 mm Hg (1.55 psi).

Comparatively, compression therapy, which uses bandages or stockings to treat deep vein thrombosis, varicose veins, and lymphoedema, come in a variety of pressures from <20 mm Hg (0.39 psi) to 60 mm Hg (1.16 psi) and above as supported by a study by Vicaretti (*Compression Therapy for Venous Disease,* 2010). As noted by Vicaretti, "The degree of compression is dependent on the condition being treated and underlying patient factors" (p. 186).

To avoid discomfort and possible skin damage (as noted by Agrawal & Chauhan, Grada & Phillips, and Scalcido, pressure should not exceed 32 mm Hg (0.62 psi). This conclusion is further supported by a study conducted by Bergstorm (*A Research Agenda for Pressure Ulcer Prevention,* 1992, as cited in Salcido et al.) and Reswick and Rogers (*Experience at Rancho Los Amigos Hospital with Devices and Techniques to Prevent Pressure Sores,* 1976), who describe pressure below 32 mm Hg (0.62 psi) as "safe".

As mentioned above, the comfortable patient pressure range of 0.05 psi to 0.65 psi can be exceeded briefly in certain circumstances, such as when performing certain critical functions or during a high-force event as described herein. For example, a critical function can include taking a radio-frequency (RF) based measurement such as tissue or lung fluid measurement. During this critical function (an RF measurement), a force applicator can be adjusted to exert a brief force resulting in pressure within a range of 0.65 to 0.68 psi, 0.68 to 0.7 psi, or 0.7 to 0.75 psi, or any user-specified range therebetween for between 2 minutes to 5 minutes. In another scenario, during such a critical function, a force applicator can be adjusted to exert a brief force resulting in pressure within a range of 0.75 to 0.77 psi for between 15 seconds to 2 minutes. In implementations, both the pressure range and the duration may be user-specified during, for example, initial device setup/baseline.

In another example, a critical function can be when the wearable medical device is about to deliver a shock to the patient via the therapy electrodes (e.g., within 10-15 seconds of actually delivering the shock; typically the device will first deploy gel in between the therapy electrode-skin interface to reduce impedance and improve efficiency of the shock energy transfer to the patient's heart). During this critical function, a force applicator can be adjusted to exert a brief force resulting in pressure within a range of 0.65 to 1.0 psi, 1.0 to 3.0 psi, 3.0 to 5.0 psi, 0.65 psi to 5.0 psi, or any user-specified range therebetween for at least the duration of the shock delivery, or about 10-15 seconds prior to and including the duration of the shock delivery. In implementations, both the pressure range and the pressure duration may be user-specified at during, for example, initial device setup/baseline.

In examples, the processor can also be configured to monitor the overall operation of the medical device for an oncoming critical function. For example, if the medical device is configured to provide one or more therapeutic shocks to the patient, the processor can detect an oncoming delivery of the shocks. In such an example, the processor can cause any components associated with the delivery of the therapeutic shocks (e.g., therapy electrodes as described herein) to increase their pressure against the skin to provide better contact during the critical function. Examples of additional critical functions that may include high-force events as described herein include detection of patient ECG parameters, calibration of the medical device during an initial fitting or subsequent adjustment, patient monitoring during high noise detection, electrode falloff detection, and/or tests of the medical device that involve acquisition of signals via the physiological sensors. Following the critical event, the processor can instruct the force applicators associated with the components associated with the critical function to return to their previous pressure levels. Such an implementation provides for more efficient and effective operation of critical functions while reducing any potential discomfort for the patient to the time immediately before, during, and immediately after the critical function.

To address these and other aspects that enhance execution of sensor-skin interface pressure monitoring for a patient wearing a wearable medical device, systems and processes configured to accurately monitor and, in some examples, adjust pressure, are described herein. For example, a wearable cardiac monitoring device can include one or more physiological sensors and associated circuitry configured to detect a physiological signal of the patient and a garment configured to be worn about a torso of the patient. The garment can include a flexible material and the one or more physiological sensors can be designed to be disposed on the flexible material. The physiological sensors can be positioned on the garment such that, when the patient wears the garment, the sensors are positioned at one or more anatomical locations of the patient's torso. The wearable cardiac device can further include one or more force applicators disposed on the flexible material proximate to the one or more physiological sensors. Each of the force applicators can be adjustable to cause a pressure (e.g., a pressure within an acceptable pressure range as described herein) to be exerted from the one or more physiological sensors on to the one or more anatomical locations of the patient's torso during the continuous, long term cardiac monitoring of the patient.

In a similar example, the wearable cardiac monitoring device can further include a medical device controller operably coupled to the one or more force applicators. In some examples, the controller can be configured to monitor a respective pressure between each of the one or more physiological sensors and a corresponding anatomical location of the patient's torso. In certain implementations, if the respective pressure at a monitored physiological sensor is out of acceptable pressure range, the controller can adjust the exerted pressure at a corresponding force applicator such that the respective pressure between the monitored physiological sensor and a corresponding anatomical location of the patient's torso is adjusted to be within the acceptable pressure range.

These examples, and various other similar examples of benefits and advantages of the techniques, processes, and approaches as provided herein, are described in additional detail below.

A patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed specialized cardiac monitoring and treatment devices, such as an MCT device, a WCD, and/or an HWD. As described above, such medical devices can benefit from the incorporation of, or interoperation with, an adjustable garment.

Figure 2:
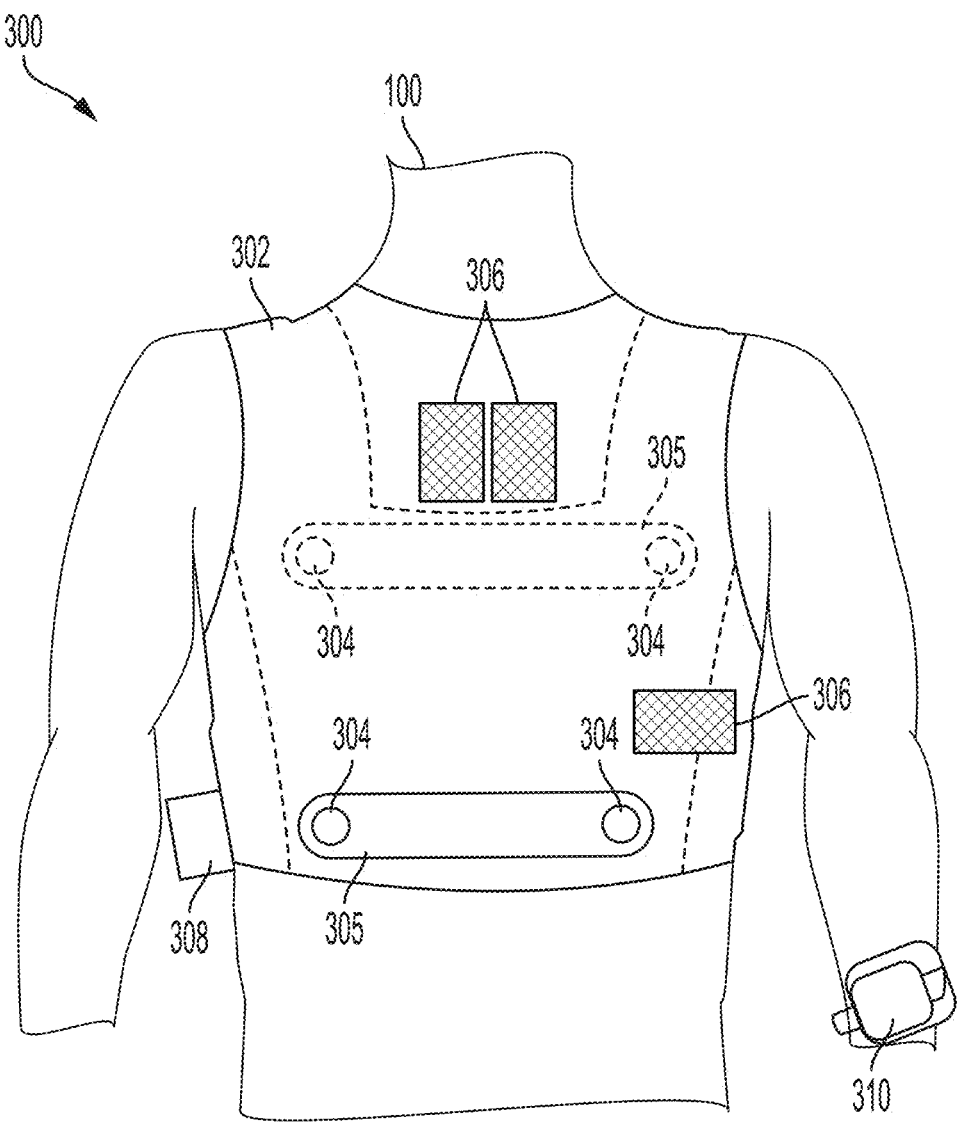
FIG. 2 illustrates a sample garment with an alternative arrangement of sensors, in accordance with an example of the present disclosure.

FIGS. 1 and 2 illustrate sample wearable medical devices 200 and 300 that include various sensors as described herein arranged about an adjustable garment as worn by a patient 100. As shown in FIG. 1, the wearable medical device 200 can include one or more components arranged about an adjustable garment 202. For example, as shown in FIG. 1, the components can include physiological sensors 204, therapy electrodes 206, and a controller 208. Additionally, the patient 100 can be wearing one or more additional physiological sensors such as a sensor 210 integrated into, for example, a wearable device such as a smartwatch.

As shown in FIG. 1, two of the physiological sensors 204 can be positioned on the front of the garment 202 and two of the physiological sensors 204 can be positioned on the back of the garment 202. Similarly, one or more of the therapy electrodes 206 can be positioned on the front of the garment 202 and two or more of the therapy electrodes can be positioned on the back of the garment 202. However, it should be noted that these positions are shown by way of example only and are intended to illustrate that various components can be arranged about the garment 202 when worn by the patient 100, thereby providing for the various components to be positioned adjacent to one or more anatomical locations on the patient 100.

As further shown in FIG. 1, each physiological sensor 204 can have an individual sensing regions 205. These regions 205 represent an area around the physiological sensors 204 and are individualized to each physiological sensor 204. In some examples, the regions 205 can have an area twice as large as the area of the corresponding physiological sensor 204. The regions 205 can be associated with a particular anatomical region at which the physiological sensor 204 is configured to be positioned. For example, the regions can include lower left chest, lower right chest, left middle back, and right middle back. As further described herein in the following discussions, a pressure measurement between one or more of the physiological sensors 204 and their associated regions 205 can be acquired, monitored, and adjusted according to the techniques and teachings described herein.

As noted above, the sensing regions 205 as shown in FIG. 1 can be individualized for each physiological sensor 204. However, in some examples, two or more of the physiological sensors 204 can be grouped together in a single sensing region.

For example, FIG. 2 illustrates a wearable medical device 300 for wearing by the patient 100. The wearable medical device 300 can include one or more components arranged about a garment 302. For example, as shown in FIG. 2, the components can include physiological sensors 304, therapy electrodes 306, and a controller 308. Additionally, the patient 100 can be wearing one or more additional physiological sensors such as a sensor 310 integrated into, for example, a wearable device such as a smartwatch.

As shown in FIG. 2, two of the physiological sensors 304 can be positioned on the front of the garment 302 and two of the physiological sensors 304 can be positioned on the back of the garment 302. Similarly, one or more of the therapy electrodes 306 can be positioned on the front of the garment 302 and two or more of the therapy electrodes 306 can be positioned on the back of the garment 302. However, it should be noted that these positions are shown by way of example only and are intended to illustrate that various components can be arranged about the garment 302 when worn by the patient 100, thereby providing for the various components to be positioned adjacent to one or more anatomical locations on the patient 100.

As further shown in FIG. 2, two or more of the physiological sensors 304 can be arranged in one or more group sensing regions 305. These regions 305 represent an area around two or more of the physiological sensors 304. The regions 305 can be associated with a particular anatomical region at which the associated physiological sensors 304 are configured to be positioned. For example, the regions can include lower chest and middle back.

Depending upon the manufacturing process and the intended wear instructions, a garment for a wearable medical device such as garments 202 and 302 as shown in FIGS. 1 and 2 and described above, can be manufactured from a variety of materials. For example, to provide a constant force against the physiological sensors such that the sensors maintain contact with a patient's body, the garment can be made from a material or a combination of materials that have elastic or other similar stretching characteristics. In some examples, the entire garment can be made from a material that is configured to be stretched and to return to its original shape. In other examples, the garment can be made from a combination of materials such that only a portion of the garment can be stretched and returned to its original shape. For example, as shown in FIGS. 1 and 2, a portion of the garment not immediately adjacent to the physiological sensors 204 and 304 can be made from one or more non-stretchable materials, while the portion of the garment immediately adjacent to the physiological sensors (e.g., in or near sensing regions 205 and 305) can be made from one or more stretchable materials.

In certain implementations, the garment can be woven from one or more materials. Depending upon the type of material used and properties of the weave of the material, the elasticity of the garment can be controlled such that areas with a tighter fabric weave are less pliant than areas with a looser fabric weave. Examples of materials that can be used to manufacture a garment as described herein can include, for example, cotton, nylon, spandex, polyester, elastin, Lycra®, and other similar natural and synthetic materials. In some examples, materials can be combined to produce a garment such as a cotton/spandex combination or a nylon/spandex combination. It should be noted, however, that these materials are provided by way of example only and various other materials can be used to manufacture a garment as described herein.

One example of a medical device that can benefit from incorporation of garments such as the adjustable garments 202 and 302 is the LifeVest® Wearable Cardioverter Defibrillator from ZOLL Medical Corporation (Chelmsford, MA). This WCD includes a garment that is configured to be worn about the torso of the patient. The garment can be configured to house various components such as ECG sensing electrodes (or other ECG sensors), therapy electrodes, one or more accelerometers configured to measure motion data for the patient, one or more audio and/or vibrational sensors configured to record vibrational signals such as cardiovibrational signals for the patient, and one or more RF sensors configured to measure RF-based physiological signals. The components in the garment can be operably connected to a monitoring device disposed within a separate housing (e.g., that may be waterproof and/or protected from ingress of dirt or other physical particles) that is configured to receive and process signals from the ECG sensing electrodes to determine a patient's cardiac condition and, if necessary, to control provision of treatment to the patient via the therapy electrodes.

Figure 3A:
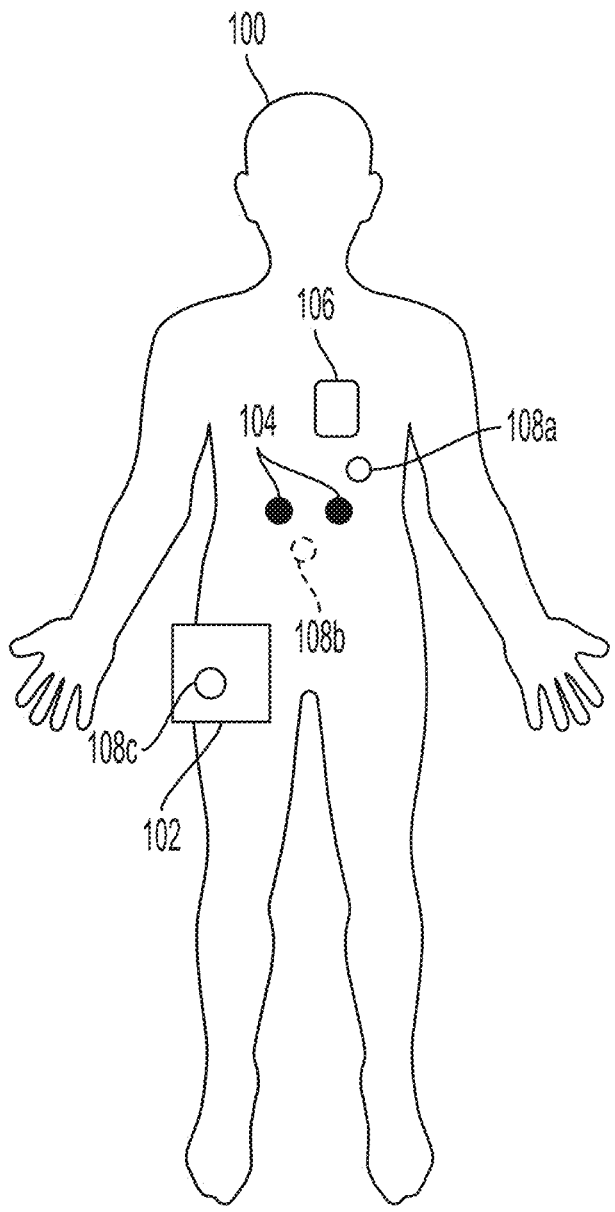
FIGS. 3A and 3B illustrate sample sensor arrangements adjustable via a garment, in accordance with an example of the present disclosure.
Figure 3B:
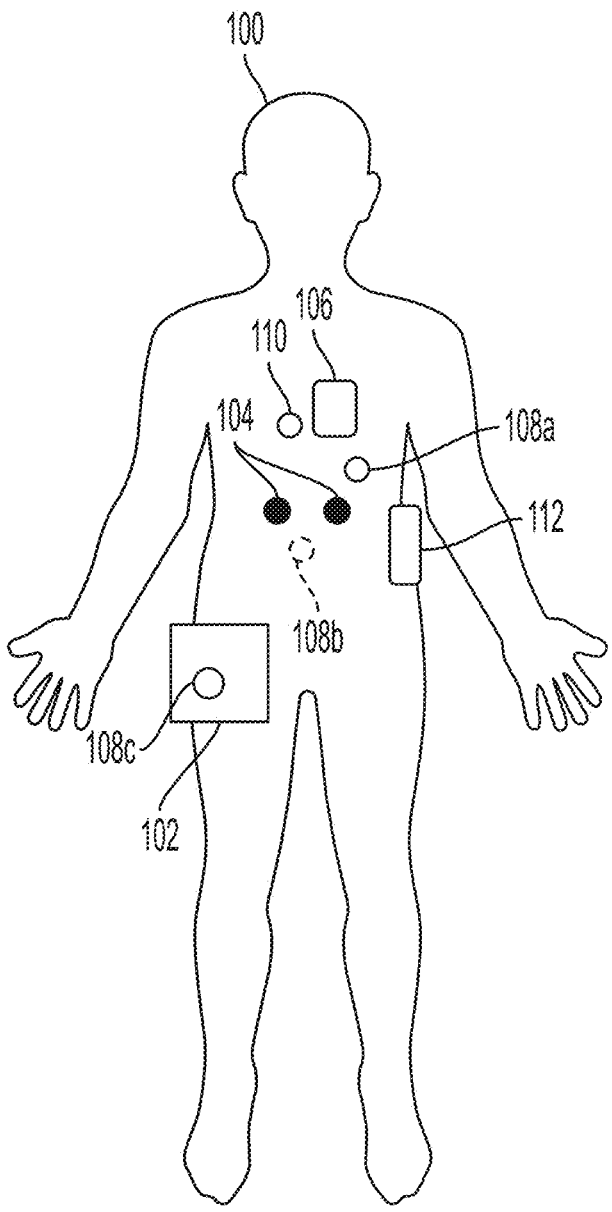

FIGS. 3A and 3B illustrate various examples of the patient 100 wearing medical devices that include one or more sensors (e.g., sensing electrodes, accelerometers, audio and/or vibrational sensors, RF sensors, stretch or pressure sensors) that can be embedded in an adjustable garment, such as the adjustable garments 202 and 302. It should be noted that accelerometers are described herein as examples of motion sensors for illustrative purposes only. In certain implementations, additional motion sensors such as gyroscopes, magnetic sensors, pressure-based motion sensors, and other similar motion sensors can be used.

As shown in FIG. 3A, the patient 100 can be prescribed an ambulatory medical device such as a WCD (or, for an in-hospital patient, an HWD). The WCD can include a controller 102 that is operably connected to one or more sensing electrodes 104 and therapy electrodes 106. Additional details of examples of the controller 102, sensing electrodes 104, and the therapy electrodes 106 can be found in the discussion of FIG. 7 below.

The WCD can also include one or more accelerometers or other motion sensors. As shown in FIG. 3A, the WCD can include three accelerometers 108a, 108b, and 108c (collectively referred to as accelerometers 108) positioned at various places on the body of patient 100. For example, accelerometer 108a can be positioned on the front of chest of the patient 100, the accelerometer 108b can be positioned on the back of the patient 100, and the accelerometer 108c can be integrated into the controller 102. Each of the accelerometers 108 can be configured to measure movement associated with the patient 100 and to output an electrical signal indicating a direction and magnitude of the movement of the patient 100.

It should be noted that the number and arrangement of the accelerometers 108 as shown in FIG. 3A is by way of example only. In certain implementations, the number and position of the accelerometers 108 can vary. Additionally, when included in a device such as a WCD, one or more of the accelerometers 108 can be integrated into components of the WCD. For example, as noted above, the accelerometer 108c can be integrated into the controller 102 of the WCD. Similarly, one or more of accelerometers 108a and 108b can be integrated into one or more components of the WCD. For example, the front accelerometer 108a can be integrated into, for example, the therapy electrode 106, which is operably connected to the controller 102 and configured to provide a therapeutic shock to the patient 100. In some implementations, the accelerometer 108a can be integrated into one of the sensing electrodes 104, which are configured to measure electrical signals produced by the patient 100 and indicative of cardiac activity of the patient 100. Similarly, accelerometer 108b can be integrated into one or more components of the WCD such as a connection node, at least one sensing electrode 104, the therapy electrode 106, and other similar components of the WCD as described herein. Alternatively or additionally, the one or more accelerometers 108 can be distinct components of the WCD.

In HWD implementations, the accelerometers can be integrated into one or more of the adhesive ECG sensing and/or therapy electrode patches. For example, a first accelerometer can be integrated into a first adhesive ECG sensing and/or therapy electrode patch and a second accelerometer can be integrated into a second adhesive ECG sensing and/or therapy electrode patch. Additional accelerometers can be disposed within a controller (similar to the controller 102 of a WCD) associated with the HWD.

In addition to accelerometers associated with a WCD as described above in regard to FIG. 3A, a patient such as the patient 100 can also wear additional sensors. As shown in FIG. 3B, the patient 100 can wear a vibrational sensor 110 that is configured to record bio-vibrational signals of the patient 100. For example, the vibrational sensor 110 can be configured to detect vibrations of the patient 100 that are associated with, for example, heart and lung activity. In certain implementations, the vibrational sensor 110 can be configured to detect cardiovibrational values including any one or all of S1, S2, S3, and S4. From these cardiovibrational values, certain heart vibration metrics or combinational metrics may be calculated, including any one or more of electromechanical activation time (EMAT), left ventricular systolic time (LVST), or percentage of left ventricular systolic time (% LVST). In some examples, the vibrational sensor 110 can be configured to detect vibrations from the cardiac system of the patient 100 and provide an output signal responsive to the detected cardiovibrational values. The vibrational sensor 110 can also include a multi-channel accelerometer, for example, a three-channel accelerometer configured to sense movement in each of three orthogonal axes such that patient movement/body position can be detected and correlated to detected cardiovibrational values. The vibrational sensor 110 can transmit information descriptive of the cardiovibrational values to, for example, a sensor interface for subsequent analysis as described below.

Additionally, the patient 100 can wear an RF sensor 112. For example, the RF sensor 112 can be configured to use RF-based techniques to assess fluid levels and accumulation in body tissue of the patient 100. For instance, the RF sensor 112 can be configured to measure fluid content in the lungs, typically for diagnosis and follow-up of pulmonary edema or lung congestion in heart failure patients. Similarly, the RF sensor can be configured to measure thoracic fluid content for the patient 100. In certain implementations, the RF sensor 112 can include one or more antennas configured to direct radio frequency waves through tissue of the patient 100 and measure output radio frequency signals in response to the waves that have passed through the tissue. In certain implementations, the output radio frequency signals include parameters indicative of a fluid level in the tissue. The RF sensor 112 can transmit information descriptive of the tissue fluid levels to a sensor interface for subsequent analysis as described below.

It should be noted that the placement and number of sensors as shown in FIGS. 3A and 3B are shown by way of example only. In actual implementation of the garment adjustment techniques as described herein, the number and position of the sensors can vary based upon the type of patient monitoring and/or treatment to be performed and other various factors.

In certain implementations, when a patient is prescribed a wearable medical device as described herein, one or more components such as physiological sensors and/or therapy electrodes are configured to be arranged about a garment for wear by the patient. For example, one or more physiological sensors and their associated circuitry are configured to be positioned at various locations on a garment such that, when worn, the sensors are positioned at one or more anatomical locations on the patient's body such as positioned at various locations about the patient's torso.

As discussed herein and noted above, a garment can include various components mounted thereon such as, for example, physiological sensors. As further discussed herein, to improve the fit and comfort of the garment, and to increase the overall efficiency and effectiveness of a physiological sensor by improving its contact with a patient's skin, a force applicator can be positioned between the garment and the physiological sensor to adjust the amount of force exerted against the sensor by the garment and/or force applicator. By adjusting the amount of force exerted against the sensor, the amount of pressure between the sensor and the patient's skin can be regulated to improve patient comfort when wearing the garment and the associated wearable medical device.

FIGS. 4A-6B illustrate various force application and sensor assemblies that can be used to attached or otherwise secure a physiological sensor to a garment while still providing for the ability to adjust the pressure between the sensor and the patient's skin as described herein.

Figure 4A:
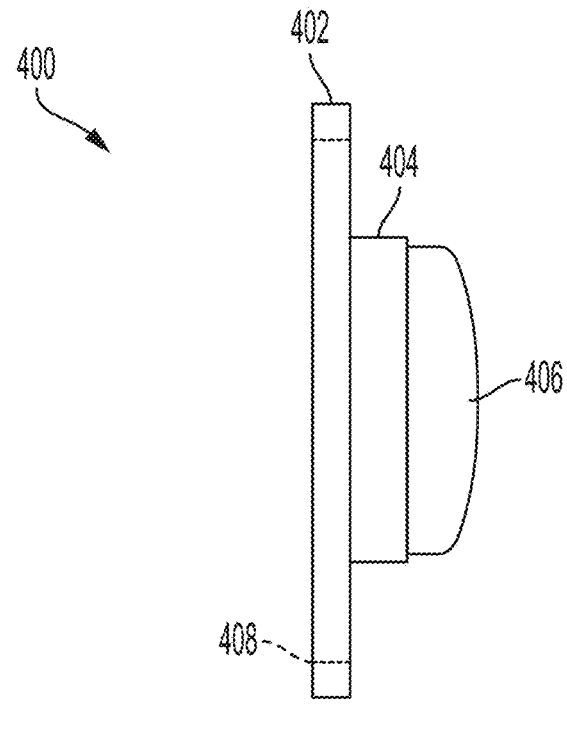
FIGS. 4A and 4B illustrate a sample arrangement of a force applicator positioned between a garment and a sensor, in accordance with an example of the present disclosure.
Figure 4B:
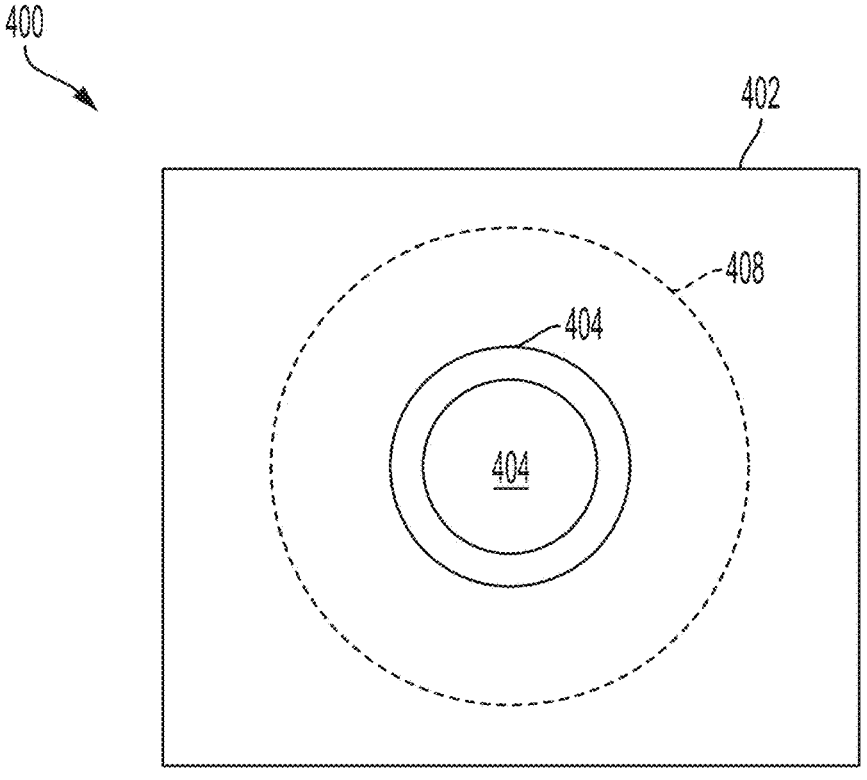

For example, FIGS. 4A and 4B illustrate an assembly 400. FIG. 4A illustrates a side view of the assembly 400, and FIG. 4B illustrates a head-on view of the assembly. As shown in FIGS. 4A and 4B, the assembly 400 includes a garment 402, a force applicator 404, a physiological sensor 406, and a reinforced garment portion 408. As shown, in assembly 400, the force applicator 404 is positioned between the garment 402 and the physiological sensor 406. As such, a force exerted by the force applicator 404 can be exerted on both the garment 402 and the physiological sensor 406. To prevent the garment 402 from stretching or otherwise displacing, thereby absorbing a large portion of the force exerted by the force applicator 404, the garment 402 can include a reinforced or rigid portion 408. The rigid portion 408 can be configured to resist deformation as a result of the force exerted by the force applicator 404, thereby resulting in the force exerted by the force applicator 404 being applied to the physiological sensor 406, increasing or otherwise adjusting the pressure between the physiological sensor 406 and the patient's skin.

In some examples, the rigid portion 408 of garment 402 can be made from a different material than the garment 402. For example, if the garment 402 is made from a generally flexible and elastic material, the rigid portion 408 can be made from a stiff or otherwise non-stretchable material such as plastic. In some examples, the rigid portion 408 can be made from the same material as the garment 402. However, the rigid portion 408 can be woven or otherwise assembled such that the flexibility or stretch of the rigid portion is lower compared to the rest of the garment 402. For example, the rigid portion 408 can be made using a tight material weave that results in reduced flexibility and stretch when compared to the rest of the garment 402, which can be made with a looser material weave.

In some examples, a garment can include one or more attachment points for providing an indication of where on the garment to attach a sensor and/or force applicator. The attachment points can be positioned about the garment such that, when the physiological sensors are disposed on the garment at the corresponding attachment points, the sensors will be properly positioned with respect to the patient's body when the patient is wearing the garment.

For example, FIG. 5 illustrates a force applicator and physiological sensor assembly 500 that includes an attachment point disposed on the garment. More specifically, the assembly 500 includes a garment 502, a force applicator 504, a physiological sensor 506, and an attachment point 508. As shown in FIG. 5, the force applicator 504 can be positioned on garment 502 at the attachment point 508. The physiological sensor 506 can then be attached or otherwise positioned adjacent to the force applicator 504. Thus, the physiological sensor 506 is positioned relatively adjacent to the attachment point 508 and, when the patient puts on the garment 502, the physiological sensor 506 will be properly positioned adjacent to the proper anatomical location on the patient's body.

In some examples, the attachment point 508 can include a reusable fastener such as a hook-and-loop fastener, an adhesive fastener, a mechanical snap fastener, or other similar mechanical interface between the garment 502 and the force applicator 504. In such an example, a portion of the mechanical fastener can be attached to the garment 502 and a corresponding portion of the mechanical fastener can be attached to the force applicator 504. For example, if the attachment point 508 uses a hook-and-loop fastener, the hook portion of the fastener can be positioned at the attachment point 508 of the garment 502, and the loop portion of the fastener can be positioned on the force applicator 504. In other examples, the attachment point 508 can be integrated into the garment 502 as a piece of the garment 502 such as a strap or pocket configured to receive at least a portion of the force applicator 504 to secure the force applicator 504 in position.

In other force applicator and sensor assemblies, the assembly can further include one or more pressure sensors configured to output a signal indicative of a measured pressure at the pressure sensor. For example, FIGS. 6A and 6B illustrate force applicator and sensor assemblies having pressure sensors.

More specifically, FIG. 6A illustrates a force application and sensor assembly 600 that includes a pressure sensor integrated into the force applicator. As shown in FIG. 6A, the assembly 600 includes a garment 602, a force applicator 604, a physiological sensor 606, an attachment point 608, a pressure sensor 610, and a wire or other similar electrical connection 612.

As shown in FIG. 6A, the force applicator 604 can be positioned on the garment 602 at attachment point 608. The physiological sensor 606 can be positioned adjacent to the force applicator 604 such that any force exerted by the force applicator 604 results in a pressure between the physiological sensor 606 and the patient's skin.

Additionally, as shown in FIG. 6A, the force applicator 604 can include an integrated pressure sensor 610 that is configured to measure and output an electrical signal indicative of the force being exerted by the force applicator 604 and the resulting pressure between the physiological sensor 606 and the patient's skin. The pressure sensor 610 can be operably connected to a controller such as the controller 102 as shown in FIGS. 3A and 3B and described above. The pressure sensor 610 can be configured to output the electrical signal to the controller via the wire 612 or another similar connector. In some examples, the wire 612 can be integrated into a single electrical connection to assembly 600 that includes, for example, electrical connections to the force applicator 604 and the physiological sensor 606 as well.

FIG. 6B illustrates another force application and sensor assembly 620 that includes a standalone pressure sensor positioned between two components of the assembly. As shown in FIG. 6B, the assembly 620 includes a garment 622, a force applicator 624, a physiological sensor 626, an attachment point 628, a pressure sensor 630, and a wire or other similar electrical connection 632.

As shown in FIG. 6B, the pressure sensor 630 can be positioned on the garment between the force applicator 624 and the attachment point 628. The physiological sensor 626 can be positioned adjacent to the force applicator 624 such that any force exerted by the force applicator 624 results in a pressure between the physiological sensor 626 and the patient's skin.

Similar to pressure sensor 610, the pressure sensor 630 can be configured to measure and output an electrical signal indicative of the force being exerted by the force applicator 624 and the resulting pressure between the physiological sensor 626 and the patient's skin. The pressure sensor 630 can be operably connected to a controller such as the controller 102 as shown in FIGS. 3A and 3B and described above. The pressure sensor 630 can be configured to output the electrical signal to the controller via the wire 632 or another similar connector. In some examples, the wire 632 can be integrated into a single electrical connection to assembly 620 that includes, for example, electrical connections to the force applicator 624 and the physiological sensor 626 as well.

It should be noted that the pressure sensor is shown as integrated into the force applicator (e.g., as shown in FIG. 6A) or positioned adjacent to the garment and force applicator (e.g., as shown in FIG. 6B) by way of examples only. In other implementations, the pressure sensor can be integrated into the physiological sensor, positioned between the force applicator and the physiological sensor, or positioned between the physiological sensor and the patient's skin, arranged such that the pressure sensor does not interfere with the electrical connection between the physiological sensor and the patient's skin.

Figure 7:
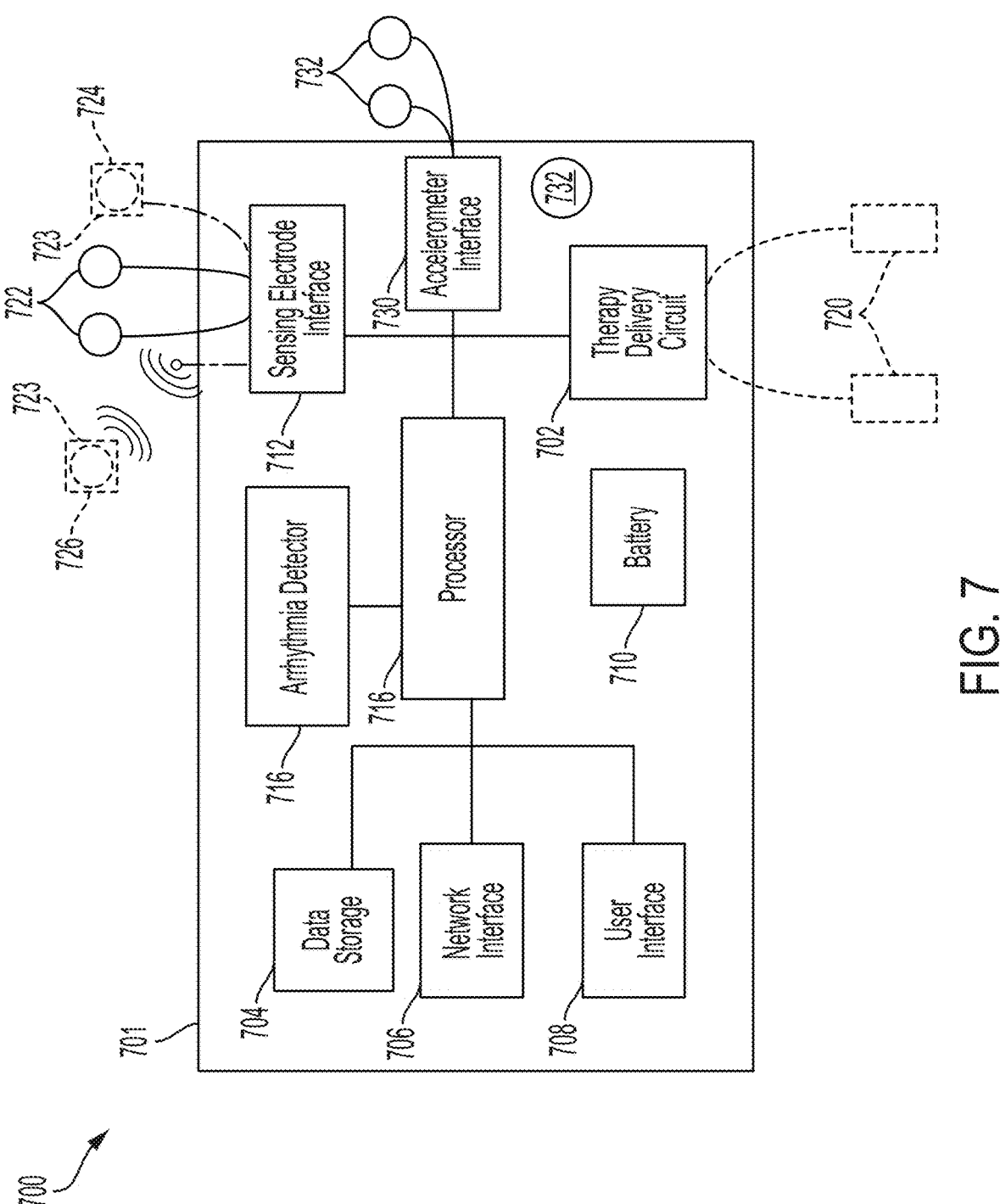
FIG. 7 illustrates a schematic view of a sample controller for a wearable medical device, in accordance with an example of the present disclosure.
Figure 8:
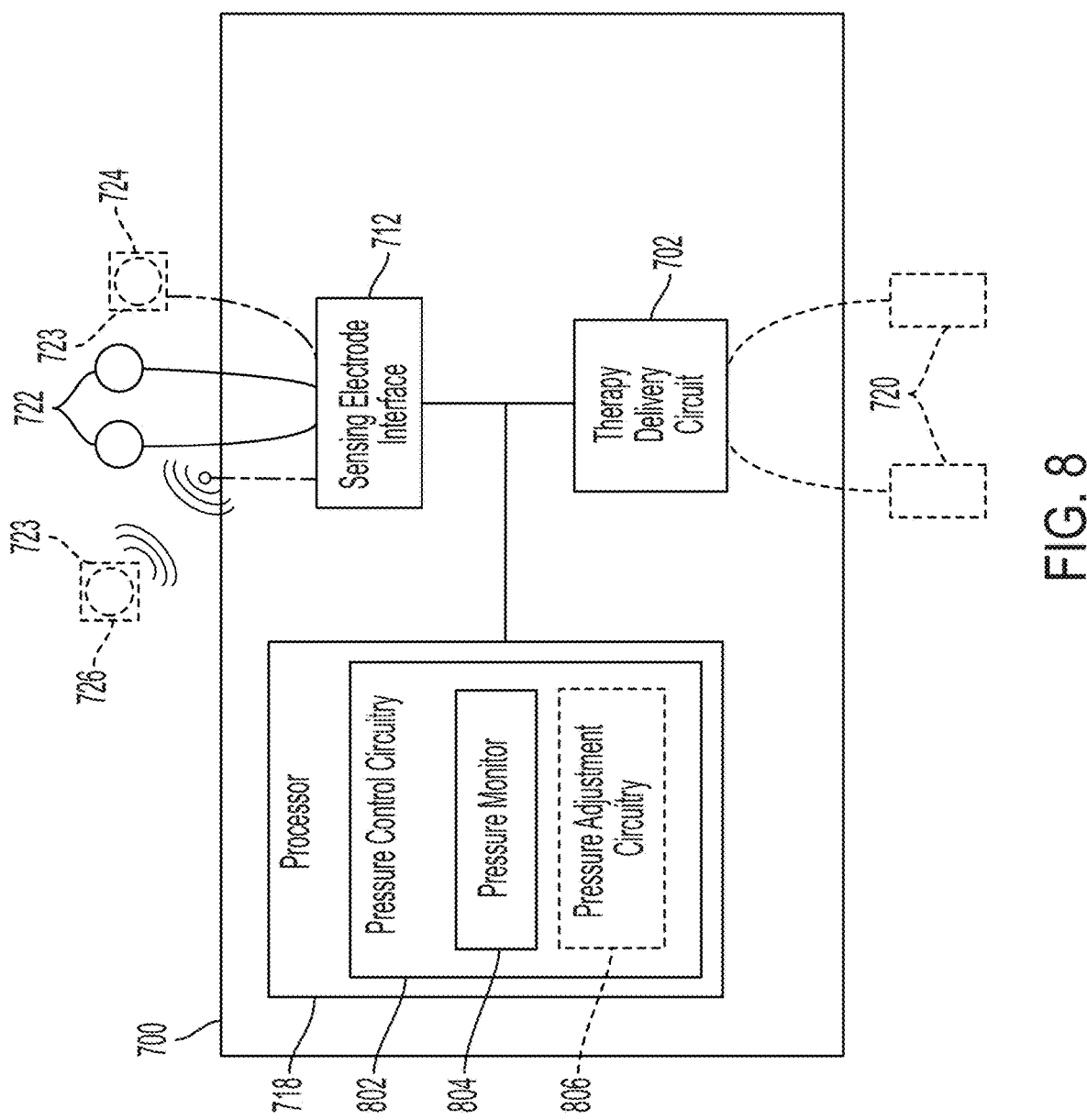
FIG. 8 illustrates a sample controller configured to monitor for exerted pressure between a sensor and a patient's skin, in accordance with an example of the present disclosure.

FIGS. 7 and 8 illustrate an example of a medical device controller 700 that is configured to control components of the medical devices described herein. Prior to describing circuitry configured to control components of adjustable garments with reference to FIG. 8, a brief introduction applicable to medical controllers in general will now be provided with reference to FIG. 7. A more detailed description of some of the components of the medical device controller 700 is provided for additional context in a sample medical device discussion further below.

FIG. 7 illustrates an example component-level view of the medical device controller 700 included in, for example, a wearable medical device such as a WCD or an HWD as described herein. The medical device controller 700 is one example of the controller 102 shown in FIGS. 3A and 3B and described above. As shown in FIG. 7, the medical device controller 700 can include a housing 701 configured to house a therapy delivery circuitry 702 configured to provide one or more therapeutic shocks to a patient via at least two therapy electrodes 720 (e.g., therapy electrode 106 as described above), a data storage 704, a network interface 706, a user interface 708, at least one rechargeable battery 710 (e.g., within a battery chamber configured for such purpose), a sensor interface 712 (e.g., to interface with both ECG sensing electrodes 722 (e.g., sensing electrodes 104 as described above) and non-ECG physiological sensors 723 such as vibrational sensors (e.g., vibrational sensor 110), lung fluid sensors (e.g., RF sensor 112), infrared and near-infrared-based pulse oxygen sensor, and blood pressure sensors, among others), a cardiac event detector 716, and at least one processor 718.

In some examples, the patient monitoring medical device can include a medical device controller that includes like components as those described above but that does not include the therapy delivery circuitry 702 and the therapy electrodes 720 (shown in dotted lines). That is, in certain implementations, the medical device can include only ECG monitoring components and not provide therapy to the patient. In such implementations, which may be referred to as MCT devices, the construction of the patient monitoring medical device is similar in many respects to the medical device controller 700 but need not include the therapy delivery circuitry 702 and associated therapy electrodes 720.

As described herein, and noted above, the present disclosure includes measuring a pressure between a sensor and the patient's skin at a sensor-skin interface and, in certain examples, automatically adjusting a force exerted upon the sensor by, for example, a force applicator as described herein such that the pressure at the sensor-skin interface is in an accepted range such as, for example, between 0.55 psi and 0.65 psi. In some examples, the accepted pressure range can include a range between about 0.60 psi and 0.62 psi. In other examples, the accepted pressure range can include a range between about 0.1 psi and 0.7 psi, 0.25 psi and 0.65 psi, 0.40 psi and 0.62 psi, and other similar pressure ranges that both provide comfort to the patient during the long-term and continuous wear of the wearable medical device as well as adequate pressure to maintain contact between the sensor and the skin, thereby resulting in more efficient and effective operation of the medical device such as improved cardiac monitoring.

More specifically, one or more components of the controller 700 can be configured to monitor the pressure at each sensor-skin interface and, in some examples, automatically adjust the pressure and/or provide an indication that the pressure at a particular sensor-skin interface is outside of the accepted range. FIG. 8 illustrates an example reduced component-level view of a medical device controller 700 in which the at least one processor 718 is configured to monitor pressure at one or more sensor-skin interfaces as described herein. For example as shown in FIG. 8, the processor 718 can include a pressure control circuitry 802. It should be noted that the pressure control circuitry 802 is shown as integrated into the processor 718. However, such a design is shown by way of example only. In certain implementations, the pressure control circuitry 802 can be integrated as a separate processing component operably coupled to the processor 718.

As further shown in FIG. 8, the pressure control circuitry 802 can include a pressure monitor 804 and, in some implementations, a pressure adjustment circuitry 806. As noted above, when a patient puts on the garment of the wearable medical device, each sensor should contact the patient's skin at or near a particular anatomical location and establish a sensor-skin interface. As further noted above in, for example, the discussion of FIGS. 6A and 6B, one or more force applicators can include a pressure sensor that is operably coupled to a monitoring device such as the controller 700. In such an example, each of the pressure sensors can be operably coupled to the pressure monitor 804. Each pressure sensor can be configured to provide pressure sensor information to the pressure monitor 804 which is then used to calculate the exerted pressure between a sensor associated with the pressure sensor and the patient's skin adjacent to that pressure sensor. Based upon this information, the processor 718 can determine and monitor the pressure at each sensor-skin interface while the patient is wearing the wearable medical device. Additional information related to monitoring the pressure at a sensor-skin interface is provided in the discussion of FIG. 9 below.

Additionally, in some implementations, the pressure control circuitry can include the pressure adjustment circuitry 806. The pressure adjustment circuitry 806 can be configured to operate in concert with the pressure monitor 804. In response to the pressure monitor 804 determining that a pressure at a sensor-skin interface is outside an acceptable range, the processor 718 may implement or otherwise cause the pressure adjustment circuitry 806 to provide a signal to one or more force applicators to adjust their output force to alter the pressure at a particular sensor-skin interface. For example, the pressure adjustment circuitry 806 can be configured to format and output a pressure control signal that is configured to cause one or more force applicators to adjust their exerted forces, thereby altering the pressure at one or more sensor-skin interfaces as described herein. Additional detail related to the adjustment of exerted forces and the resulting sensor-skin interface pressures is provided in the discussion of FIGS. 10A and 10B below.

It should be noted that the pressure monitor 804 and the pressure adjustment circuitry 806 are shown as separate components by way of example only. In certain implementations, the pressure monitor 804 and the pressure adjustment circuitry 806 can be implemented as a single processing component within the pressure control circuitry 802.

As noted above, in order to properly monitor the pressure at each sensor-skin interface, one or more pressure sensors can be used to provide a monitoring component such as the pressure monitor 804 with one or more electrical signals related to the pressure at each interface. To properly provide an accurate signal, the various pressure sensors and force applicators can be calibrated by the manufacturer of the wearable medical device and garment such that the signals as provided by the pressure sensors are reflective of the current pressure at each interface.

To provide for such a calibration, the force applicators and pressure sensors as described herein can be subjected to a level of testing, monitoring, and adjustment. Similarly, the instructions performed by the processor 718 in concert with the pressure monitor 804 can be adjusted to provide further calibration and higher accuracy when monitoring the pressures at the one or more sensor-skin interfaces.

As the device described herein is a wearable device, it is valuable to monitor and record the magnitude and location of pressure on the patient's body when worn as well as monitor the signal quality that is received from various physiological electrodes at various pressures. Generally, for patient comfort and safety, the pressure at any one sensor-skin interface should be kept around 0.62 psi or lower to avoid discomfort such as pressure ulcers. In some examples, provided signal quality from the physiological sensors does not suffer, the pressures can be kept at or around 0.30 psi at each sensor-skin interface.

To calibrate, a pressure sensor such as a Tactilus® pressure pad, manufactured by Sensor Products Inc. of Madison New Jersey, can be used to measure pressure at various locations on a patient's body and to provide calibration information regarding the force applicators and associated pressure sensors. Generally, a pressure pad is a sheet of fabric encasing an array of pressure sensors and wiring that can measure pressure over complex surfaces. For the garment as described herein, a pressure pad can be used to find the amount of pressure exerted by one or more force applicators onto one or more physiological sensors when the garment is worn, thereby mapping sensor-skin interface pressure to a particular exerted force value for each force applicator.

To perform the test, the garment is populated with the various components as described herein and placed on either a mannequin or a human test subject. The pressure pad is then placed under the garment, between the garment and the test subject's skin. The pressure pad is thus configured to collect pressure information from both the areas of interest (e.g., immediately proximate physiological sensors) as well as other areas of the garment. The testing can be used to evaluate comfort qualitatively while both providing feedback on force applicator and pressure sensor calibration as well as provide inspiration for improved garment design.

To run a test, an application associated with the pressure pad can be configured to monitor pressure exerted on the pressure pad at various locations and under various conditions. To prepare the test subject, if a human, the garment can be put on the test subject and fitted properly as would be done for a patient. If a mannequin is used, a synthetic skin substitute such as a neoprene wet suit can be used to simulate the elasticity of human skin. The garment can then be properly fitted to the mannequin.

Additional information can also be associated with a sample test such as a garment ID, subject information (e.g., mannequin, human body, identification and sizing information), state of the garment (e.g., pre-wear, post wear, or post-wash).

To perform a test of a specific anatomical region (e.g., front of garment between garment and chest), the following test steps can be performed. Initially, a test application is opened, the pressure pad is operably connected to the computing device running the test application, and, if needed, the pressure pad can be calibrated. The garment is also assembled such that any component associated with the garment is properly placed and secured.

Once the garment is assembled, the garment is placed on the test subject. One or more adjustable features of the garment such as clasps are set to a particular fit level such as a loose fit for the initial test. The pressure pad is positioned such that it is between one or more pressure causing components in the area of testing. The tester runs a scan using the pressure pad application, and all relevant pressure data is recorded by the application. The tester can name the results accordingly, e.g., "Front Loose."

After the first test, the garment is adjusted from the loose fitting to a tight fitting and the scan is run again. After the second scan, the application records all relevant pressure data for the second scan. The tester then moves the pressure pad to a second area of interest and repeats the scan at that area for both a loose fitting garment and a tight fitting garment. This is repeated for all areas of interest.

Figure 15:
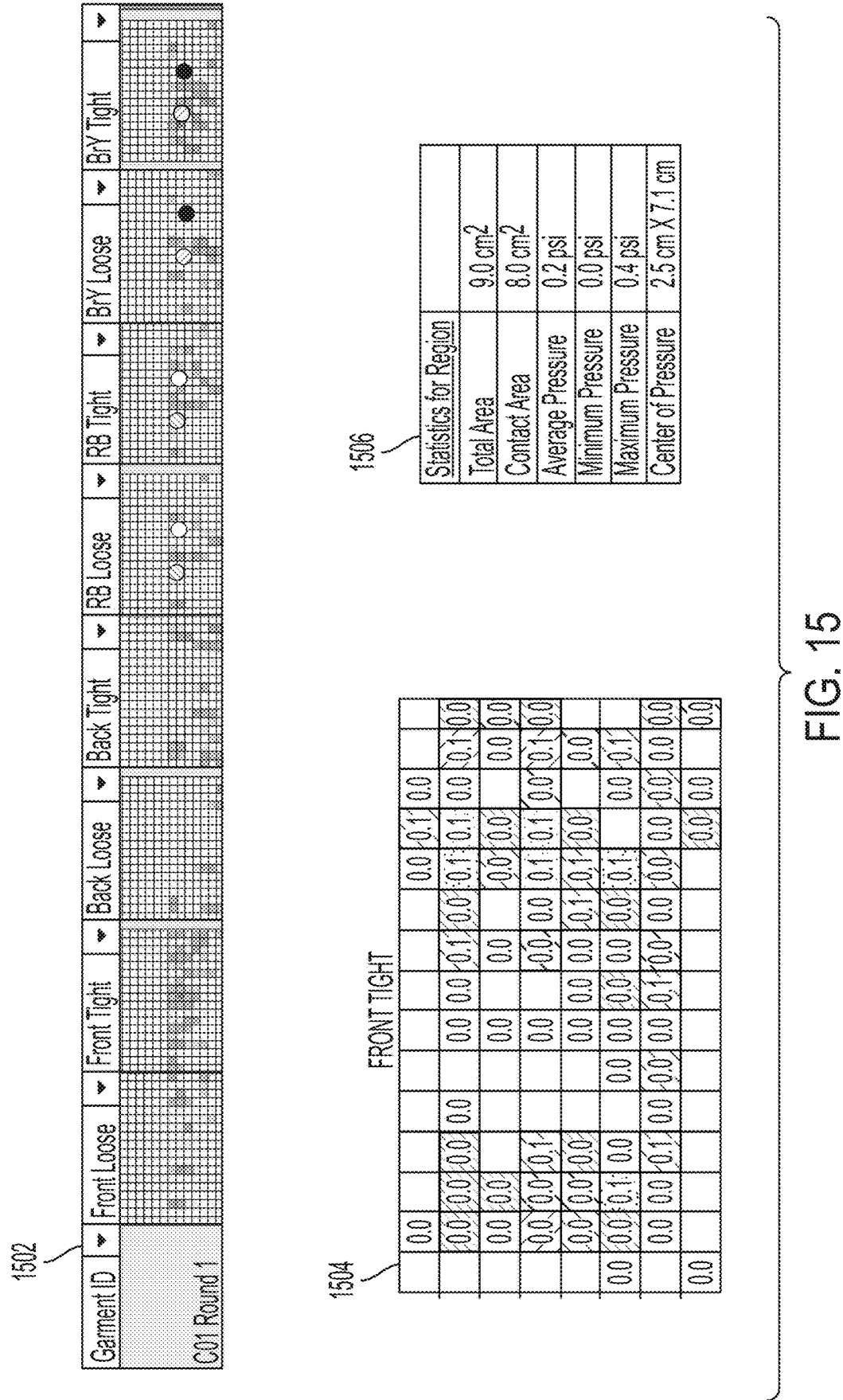
FIG. 15 illustrates sample calibration and monitoring testing data, in accordance with an example of the present disclosure.

Upon completion of the pressure pad testing, the pressure pad application can produce a set of results in a particular data structure such as a spreadsheet. As shown in FIG. 15, results 1502 includes a set of results for various scans. During review, the tester can access more detailed plots for each set of test results. For example, as shown in FIG. 15, results 1504 includes a more detailed view of the pressure pad pressure levels during the front tight test. Additionally, the tester, or someone reviewing the test data, can see a set of statistics 1506 related to a test such as total area tested, contact area measured, average measured pressure, minimum measured pressure, maximum measured pressure, center of pressure information, and other similar information received from the pressure pad and collected by the pressure pad application.

Figure 16A:
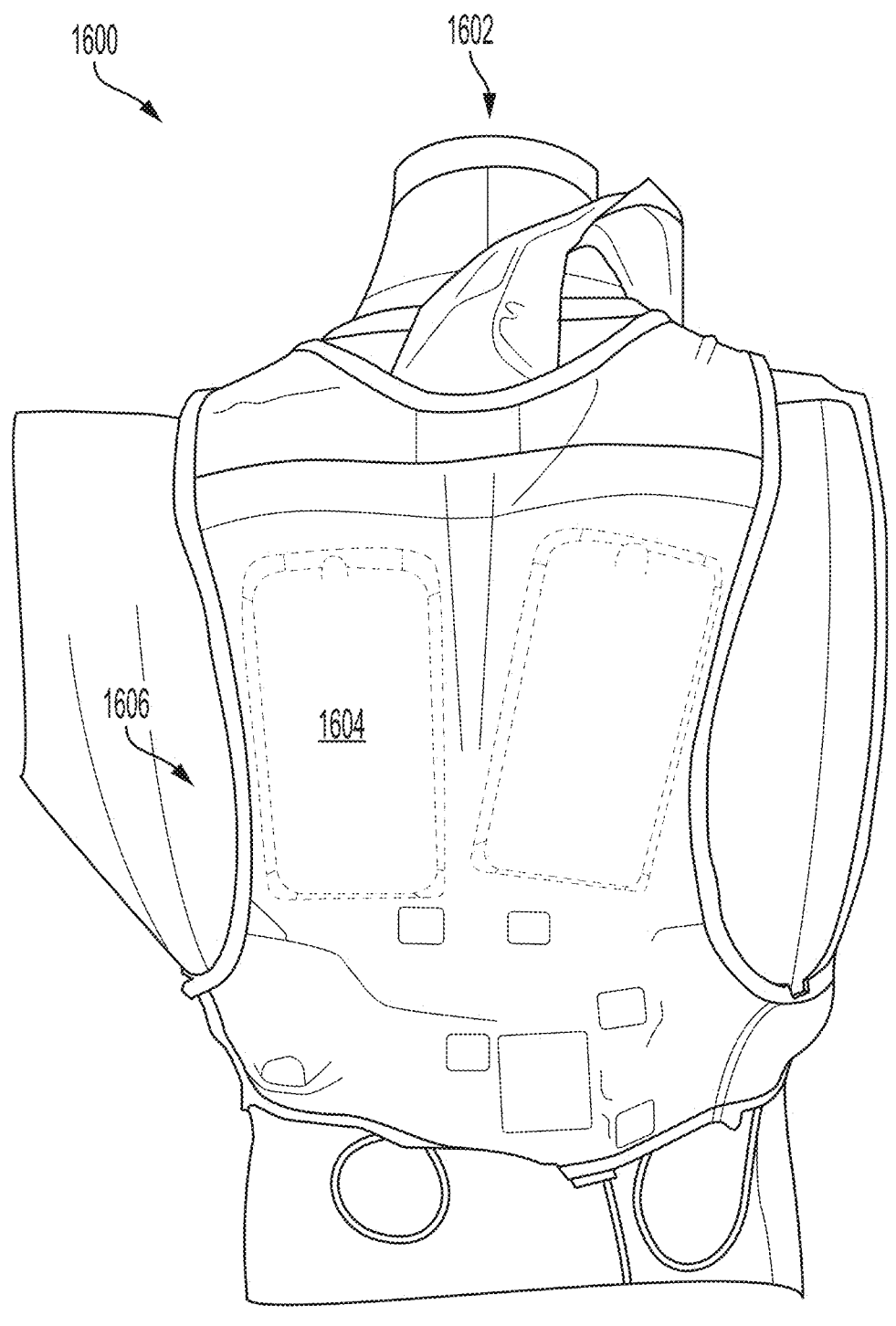
FIGS. 16A and 16B illustrate a test setup for measuring exerted force by a medical device garment, in accordance with an example of the present disclosure.
Figure 16B:
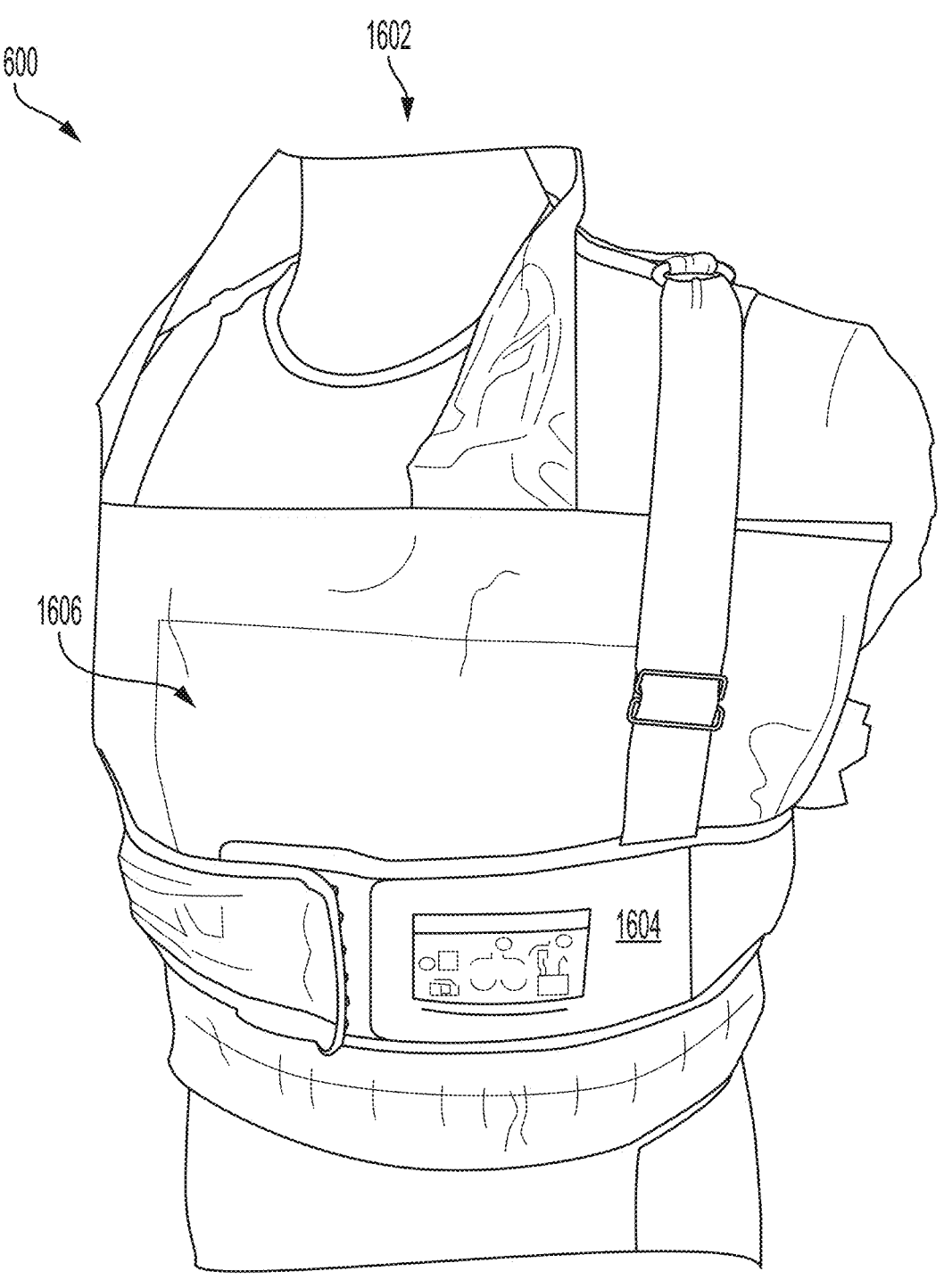

FIGS. 16A and 16B illustrate a sample external pressure measurement device configured to measure pressure exerted by a medical device garment and to provide pressure results such as those shown in, for example, FIG. 15 as described above. For example, as shown in FIG. 16A, the external pressure measurement device 1600 can include a mannequin structure 1602 that is configured to simulate a patient's body. The mannequin structure can be configured to receive the wearable medical device 1604 and simulate the device as being worn by a patient. A pressure sensor pad 1606 as described above can be placed between the wearable medical device 1604 and the mannequin 1602. The pressure sensor pad 1606 can include, for example, an array of pressure sensors configured to measure a pressure exerted by the wearable medical device 1604 as exerted on various locations on the mannequin 1602. The pressure sensor pad 1606 can be operably connected to a computing device that is configured to receive output signals form the pad and to process the signals into a set of results such as those shown in FIG. 15 and described above.

FIG. 16B illustrates an alternative setup for the external pressure measurement device 1600. To provide a complete measurement of the pressure exerted by the wearable medical device 1604, the pressure sensor pad 1606 can be repositioned at additional locations between the wearable medical device and the mannequin 1602. As shown in FIG. 16B, the pressure sensor pad has been moved to the front of the mannequin 1602 to measure pressure sample pressures exerted on the patient's chest (as simulated by the mannequin) as exerted by the wearable medical device 1604.

In certain implementations, based upon the results as provided by the pressure pad application, the pressure information can be compared to measured pressure values as received from pressure sensors integrated into the garment, e.g., pressure sensors integrated into the force applicators or positioned adjacent to the force applicators and/or physiological sensors as described herein. This information can be used to determine a correlation between force exerted by one or more force applicators and resulting pressures at an associated sensor-skin interface. Additionally, the information can be used to calibrate the force applicators and pressure sensors. For example, the pressure monitor (e.g., pressure monitor 804 as described herein) can be configured to adjust or otherwise interpret signals from the pressure sensors based upon the test information such that any signals received from the pressure sensors are properly interpreted and/or scaled if needed to accurately reflect the pressure value at a particular sensor-skin interface. Additionally, such testing can provide a baseline pressure measurement collected under ideal, or nearly ideal, circumstances that can be used by the processor in combination with the pressure monitor component to measure and adjust sensor-skin interface pressures when the garment is being worn by the patient in real time as described herein.

Figure 9:
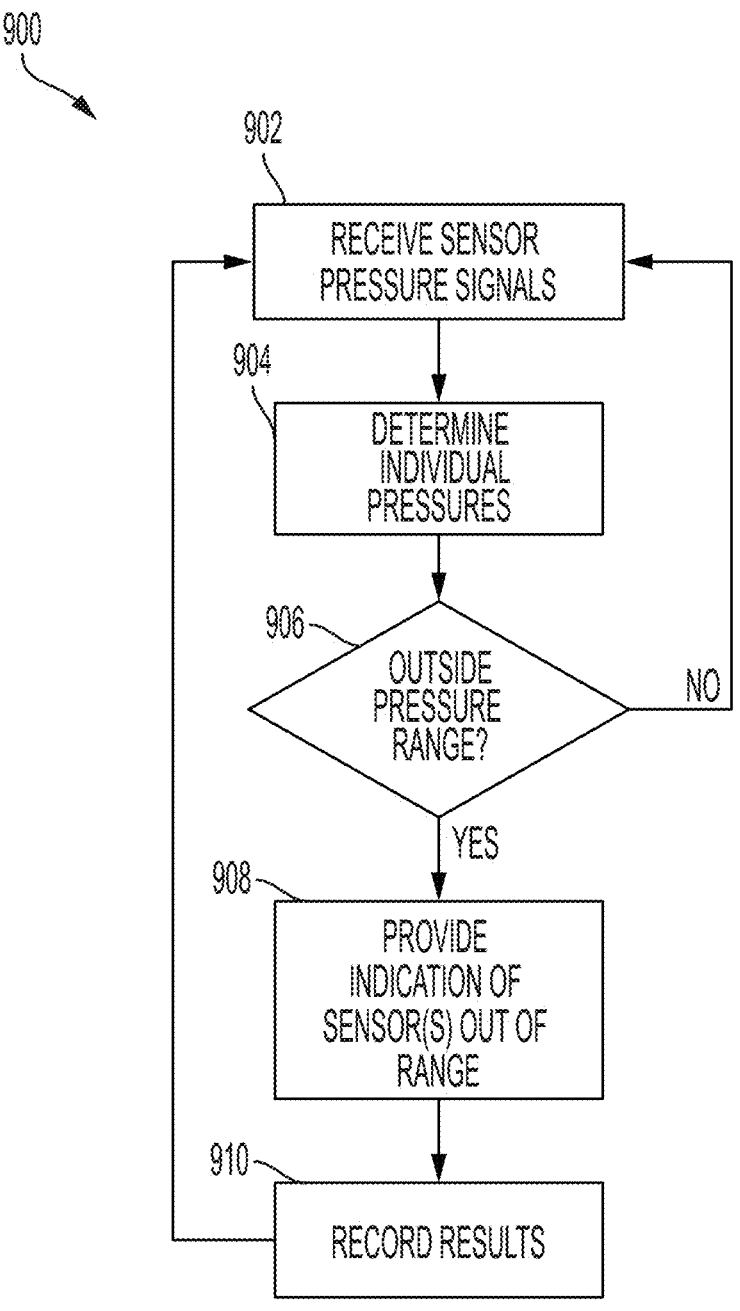
FIG. 9 illustrates a sample process flow for monitoring exerted pressure at one or more sensors, in accordance with an example of the present disclosure.
Figure 10A:
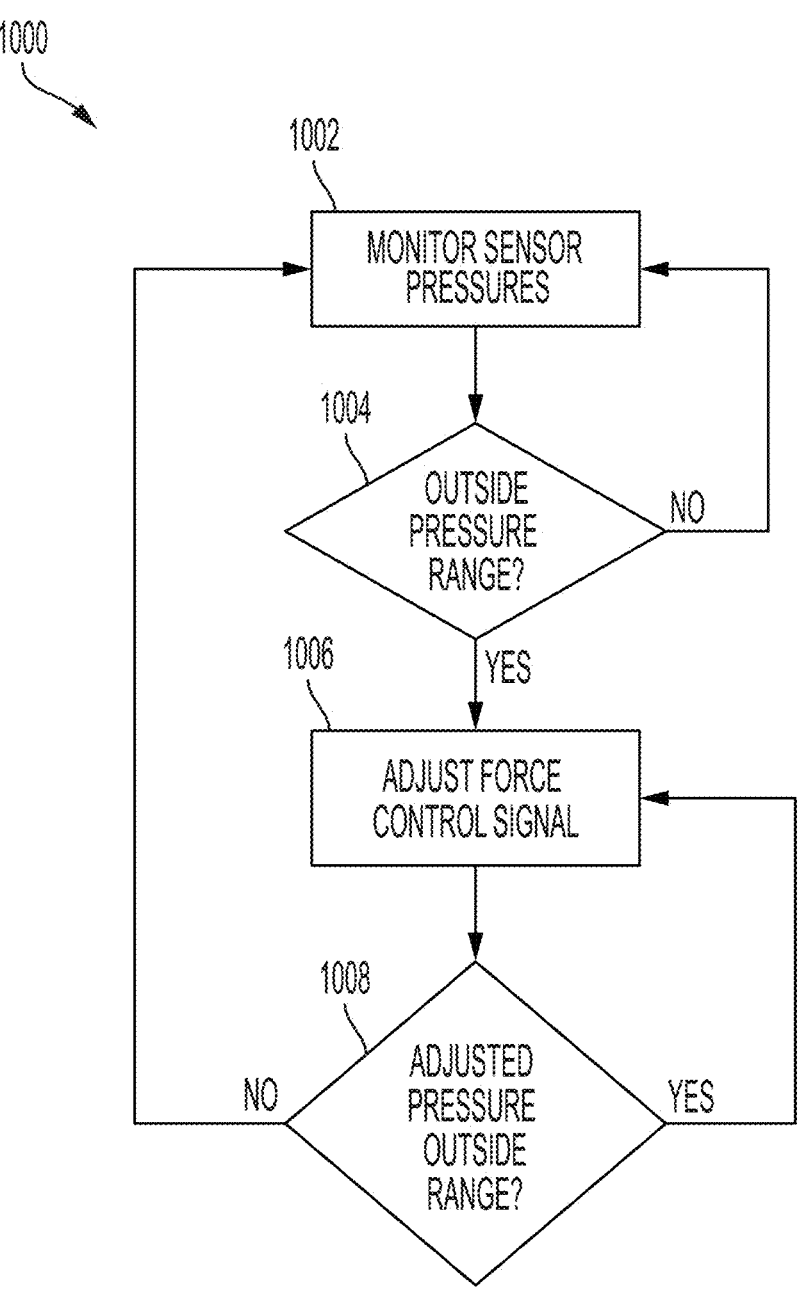
FIGS. 10A and 10B illustrate sample process flows of monitoring for and adjusting exerted pressure at one or more sensors, in accordance with an example of the present disclosure.
Figure 10B:
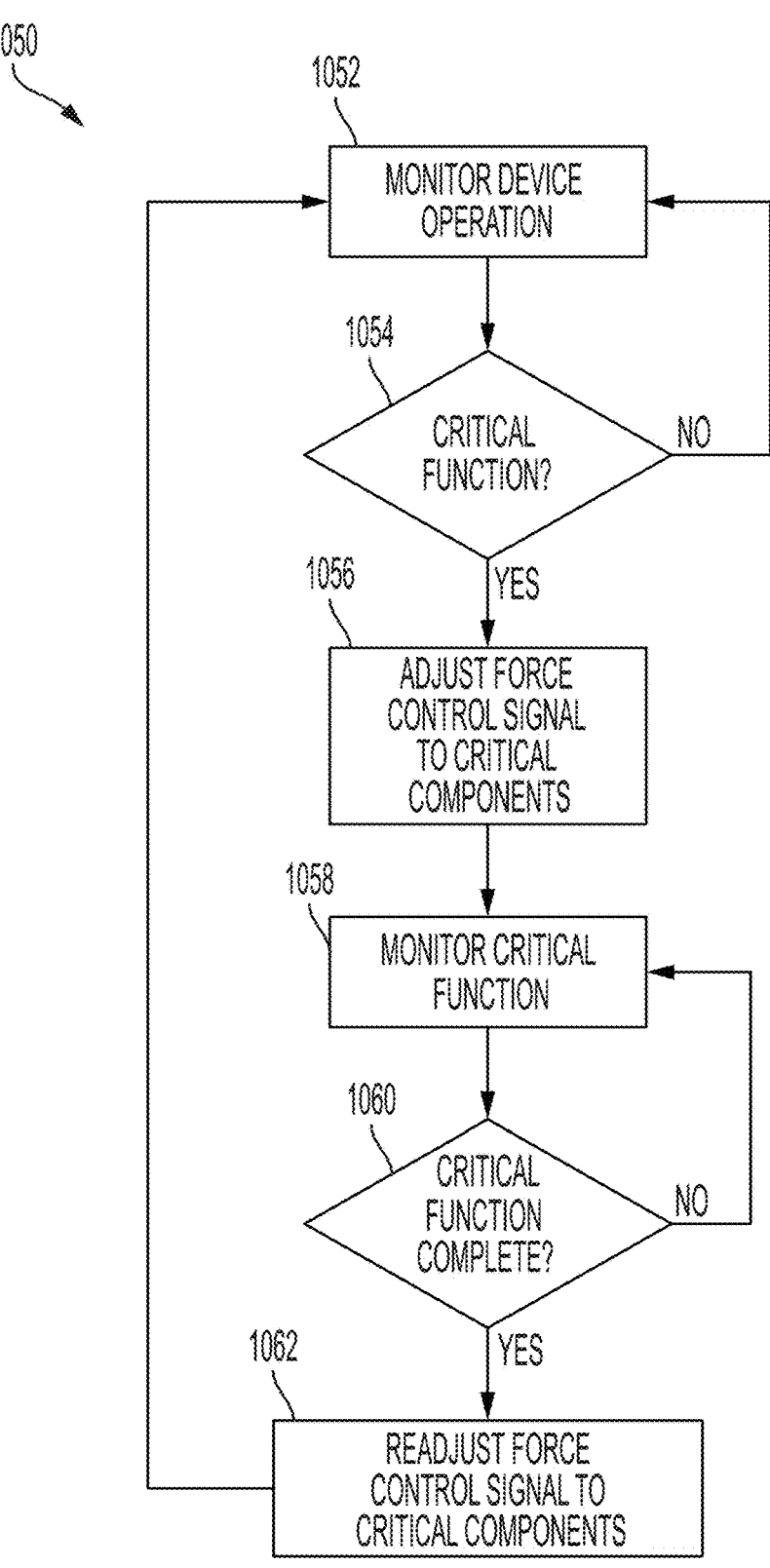
Figure 11:
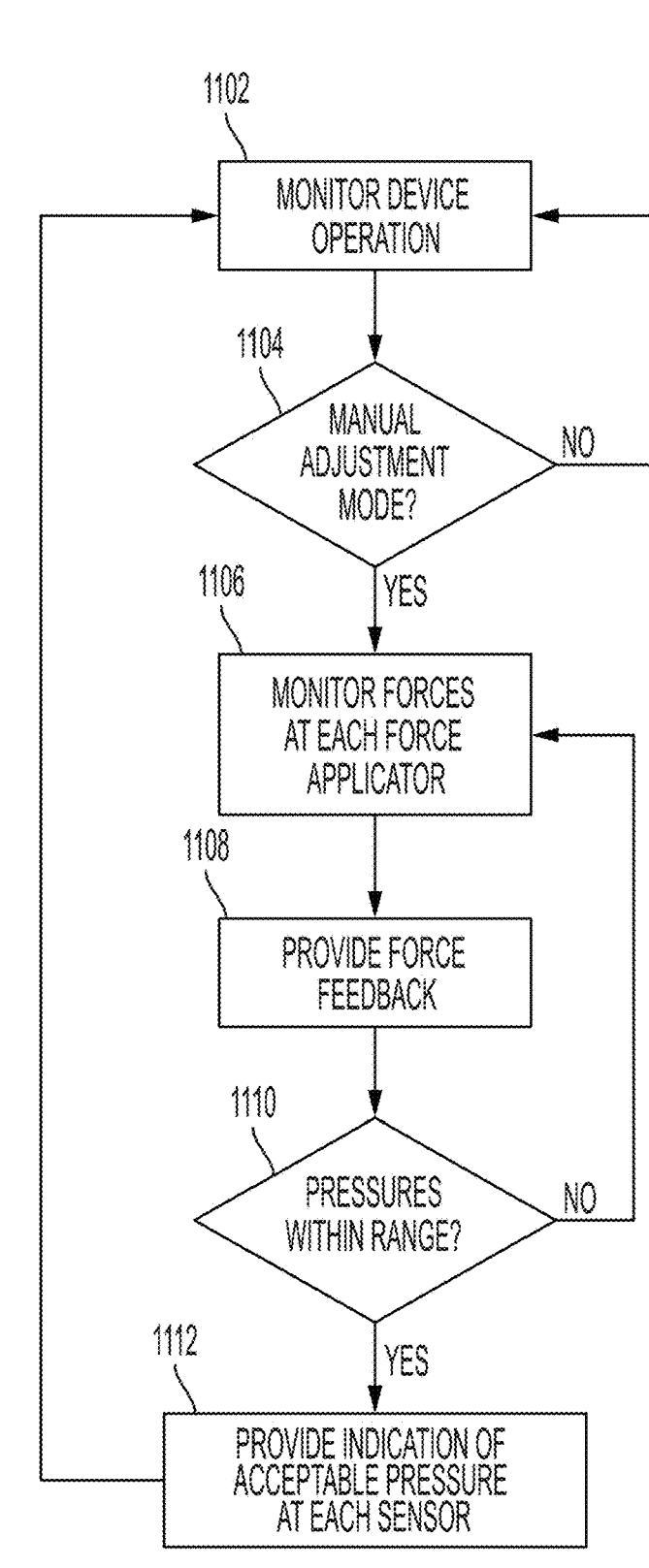
FIG. 11 illustrates a sample process flow of monitoring a manual adjustment of pressure at one or more sensors, in accordance with an example of the present disclosure.

As described herein, a medical device controller such as the controller 700 can be configured to monitor the pressure between one or more physiological sensors and patient's skin at one or more sensor-skin interfaces. Based upon the monitored pressure, the controller can be configured to provide feedback information regarding the monitored pressure and/or automatically adjust one or more force applicators to adjust the pressure at the one or more sensor-skin interfaces. FIGS. 9-11 illustrate various process flows detailing various processes for monitoring and/or adjusting pressure at one or more sensor-skin interfaces by adjusting the force exerted by one or more force applicators. Each of the processes as shown in FIGS. 9-11 can be implemented, for example, by a processor of a medical device controller such as processor 718 of medical device controller 700, working in concert with the pressure control circuitry 802 as described above.

For example, FIG. 9 illustrates a sample process 900 for monitoring the pressure at each sensor-skin interface when a patient is wearing a wearable medical device such as those described herein. As shown in FIG. 9, the processor can receive 902 sensor pressure signals from each sensor-skin interface, the sensor pressure signals as measured by the pressure sensors at each force applicator sensor assembly. The processor can process the pressure signals and determine 904 one or more individual pressures at each sensor-skin interface. The processor can then compare the determined individual pressures to an acceptable pressure range and determine 906 if the pressure is outside the acceptable range. For example, the acceptable pressure range can be between about 0.55 psi and 0.62 psi between a physiological sensor and the patient's skin.

As further shown in FIG. 9, if the processor determines 906 that the individual pressures are within the acceptable pressure range, the processor can continue to receive 902 the sensor pressure signals. Conversely, if the processor determines 906 that the individual pressures are outside the acceptable pressure range, the processor can provide 908 an indication/alert that one or more sensor-skin interfaces are outside the acceptable pressure range. For example, the processor can provide 908 an audio and/or visual alarm indicating that the one or more sensor-skin interfaces are outside of the acceptable range. The processor can also record 910 the results for further analysis. For example, if the same force applicator and sensor assembly is outside the acceptable pressure range regularly (e.g., more than 5 times per day), the manufacturer of the wearable medical device can analyze the recorded information to determine that there may be a problem with the garment and/or the force applicator that is causing the unacceptable results. After recording, the processor can continue to receive 902 the sensor pressure signals and repeat process 900.

As noted above, the pressure control circuitry 802 can include pressure adjustment circuitry 806 that can be configured to provide a control signal to one or more force applicators to adjust their exerted forces, thereby altering the pressure exerted by a corresponding physiological sensor on the patient's skin. FIGS. 10A and 10B illustrate processes that can be incorporated to automatically adjust the pressure at one or more sensor-skin interfaces by altering or otherwise adjusting a control signal to one or more force applicators as described herein.

For example, FIG. 10 illustrates process 1000 for monitoring and automatically adjusting the pressure at one or more sensor-skin interfaces. As shown in FIG. 10A, the process 1000 can include the processor monitoring 1002 the sensor pressures at one or more sensor-skin interfaces using, for example, a process such as process 900 as shown in FIG. 9 and described above.

As further shown in FIG. 10A, based upon the monitoring of the sensor-skin interface pressures, the processor can determine 1004 if one or more individual pressures are outside the acceptable pressure range. If the processor determines that there are not any individual pressures outside the acceptable pressure range, the processor can continue to monitor 1002 the sensor pressures. If, conversely, the processor does determine 1004 that there are one or more individual pressures outside of the acceptable pressure range, the processor can adjust 1006 a force control signal associated with the force applicator that corresponds to the sensor-skin interface that is outside the acceptable pressure range. For example, if the sensor-skin interface is above the acceptable pressure range, the processor can adjust 1006 the control signal for the corresponding force applicator to lower its exerted force. Conversely, if the sensor-skin interface is below the acceptable pressure range, the processor can adjust 1006 the control signal for the corresponding for applicator to increase its exerted force.

Once the exerted force has been adjusted, the processor can determine 1008 if the pressure at the adjusted sensor-skin interface is still outside the acceptable pressure range. If the processor does determine 1008 that the adjust pressure is still outside the acceptable pressure range, the processor can further adjust 1006 the force control signal. If, however, the processor determines 1008 that the adjust force is now within the acceptable force range, the processor can continue to monitor 1002 the sensor-skin interface pressures.

In some examples, the processor can also be configured to monitor 1002 the physiological sensors for noise or other similar feedback on signals received from the sensors. Such noise can indicate a poor connection between the physiological sensor and the patient's skin due to, for example, patient movement or the current position of the garment on the patient. In such an example, the processor can further adjust 1006 the force signal to tighten one or more physiological sensors against the patient skin until the noise is reduced or otherwise eliminated. If the added exerted force results in the pressure at the sensor-skin interface exceeding the acceptable pressure range, the processor can monitor signal quality while slowly lowering the pressure back to an acceptable value.

Additionally, a wearable medical device as described herein can be configured to perform various critical operations. For example, critical operations can include providing one or more therapeutic shocks (e.g., defibrillation and/or pacing shocks) to the patient via one or more therapy electrodes, performing RF-based monitoring of one or more physiological metrics, performing ECG metric or other similar cardiac metric monitoring, performing cardio-vibrational monitoring, performing patient monitoring during a high noise detection, monitoring a patient when a sensor falloff event is detected (e.g., one or more ECG sensors lose contact with the patient's skin as described herein), and other similar high-force events. During such an operation, it may be beneficial to increase the force being exerted on a component involved in the critical operation to ensure that the component maintains good contact with the patient's skin. In some examples, the force exerted on a critical component can be increased for a brief period of time during the critical or high-force event. For example, if a normal pressure range is about 0.05 psi to about 0.65 psi, during the high-force event the exerted pressure range can be increased to about 0.65 psi to about 5.0 psi during the high-force event. In some examples, the critical or high-force event can span a brief period of time including, for example, 5 seconds, 10 seconds, 15 seconds, 20 seconds, 25 seconds, 30 seconds, 45 seconds, and 60 seconds. As such, the systems and methods as described herein can be used to increase the force exerted on a critical component during a critical operation.

More specifically, FIG. 10B illustrates a process 1050 that includes monitoring for a critical operation and responding accordingly as described above to increase the force exerted on a critical component. As shown in FIG. 10B, the process can monitor 1052 the wearable medical device for particular operations. During monitoring, the processor can determine 1054 if the medical device is performing a critical function. If the processor does not determine 1054 that the device is performing a critical operation, the processor can continue to monitor 1052 the device operation. Conversely, if the processor does determine 1054 that the device is performing a critical operation, the processor can adjust 1056 the force control signal for any force applicators associated with a critical component operating during the critical function such that the pressure between the critical component and the patient's skin is increased during the critical operation.

As further shown in FIG. 10B, the processor can monitor 1058 the critical operation and the operation of the device to determine 1060 if the critical function is complete. If the processor determines 1060 that the critical function is not complete, the processor can continue to monitor 1058 the critical function. If, however, the processor does determine 1060 that the critical function is complete, the processor can readjust 1062 the force control signal such that the force applicators associated with the one or more critical components return to their previous levels of exerted forces, thereby reducing the pressure between the critical components and the patient's skin to a previous level (e.g., the level prior to the critical function starting).

In addition to automatic adjustment of the pressure at one or more sensor-skin interfaces as described herein, someone such as a caregiver or a person helping a patient get fitted for a wearable medical device may want to manually adjust the force exerted by one or more force applicators so that they can calibrate or otherwise setup the wearable medical device when first worn by the patient. In such an example, the techniques as described herein can be used to monitor the pressure at one or more sensor-skin interfaces and provide feedback to the caregiver or person helping the patient. For example, FIG. 11 illustrates process 1100 that includes monitoring and providing feedback on sensor-skin interface pressures during a manual adjustment of the wearable medical device.

More specifically, as shown in FIG. 11, process 1100 can include the processor monitoring 1102 the device operation mode to determine 1104 if the device is in a manual adjustment mode. If the processor determines 1104 that the device is not in a manual adjustment mode, the processor can continue to monitor 1102 operation of the device. If, however, the processor does determine that the device is in a manual adjustment mode, the processor can monitor 1106 the forces being exerted at each force applicator and the resulting sensor-skin interface pressure associated with each monitored exerted force. Based upon the monitored forces, the processor can provide 1108 force feedback to the person manually adjusting the device. For example, the feedback can include an audio or visual signal that indicates the pressure at one or more sensor-skin interfaces. For example, the feedback can include an indication that the force being exerted by one or more force applicators should be increased or decreased accordingly to adjust the pressure at a corresponding sensor-skin interface as described herein. Additionally, the processor can determine 1110 if the pressures at each sensor-skin interface are within an acceptable range. If the processor determines 1110 that the pressures are not within an acceptable range, the processor can continue to monitor 1106 the forces at each force applicator. Conversely, if the processor does determine 1110 that the sensor-skin interface pressures are within an acceptable range, the processor can provide 1112 an indication of the acceptable pressure at each sensor-skin interface.

It should be noted that the individual sensor-skin interface monitoring steps as shown in FIG. 11 can be performed in a sequential order such that each individual interface and associated components such as the associated force applicator are monitored and evaluated individually. Process 1100 as shown in FIG. 11 includes monitoring each sensor-skin interface in a single process flow by way of example only.

In some examples, when performing the process 1100 as shown in FIG. 11, the processor can be further configured to collect or otherwise analyze patient feedback regarding, for example, patient comfort. Based upon this information, the processor can determine whether one or more sensor-skin interface pressures can be lowered to provide the patient added comfort while still monitoring the resulting adjusted pressure to determine if the adjusted pressure is still within the acceptable pressure range, thereby providing for a high quality signal form the associated physiological sensor while still providing patient comfort.

Additionally, it should be noted the process flows as shown in FIGS. 9-11 are shown by way of example only. Depending upon the design and implementation of the systems, devices, processes, and methods as described herein, the individual process flows can be altered accordingly to accommodate changes resulting from differences in designs. For instance, the processes described herein can be executed locally within a medical device and/or remotely from the medical device (e.g., in data processing devices such as remote server systems that are in communication with or otherwise associated with the medical device). Thus, at least some steps of the processes described herein can be executed on a server and one or more of the results of such steps can be implemented by the medical device.

Figure 17A:
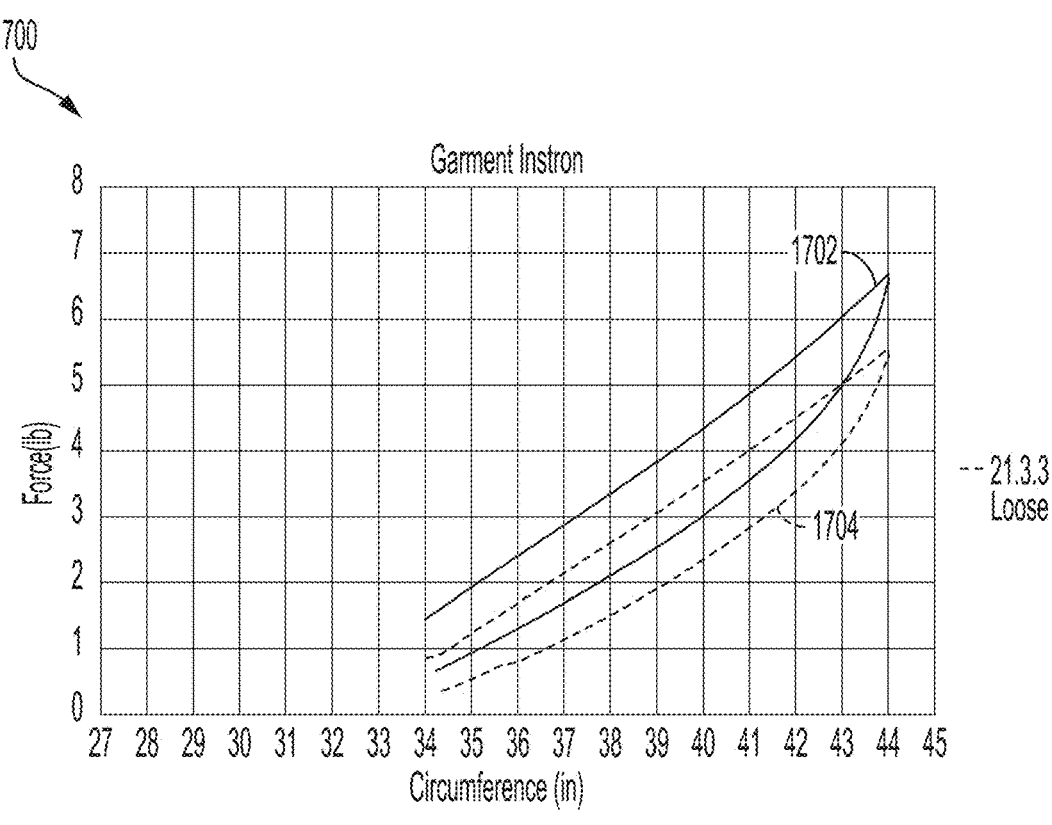
FIGS. 17A and 17B illustrate sample plots depicting force and pressure curves for sample medical device garments, in accordance with an example of the present disclosure.

In certain implementations, to provide accurate pressure measurements, the one or more force applicators and pressure sensors as described herein can be calibrated to measure exerted pressure. For example, each garment as described herein can be configured to have a specific force profile that illustrates a constant or average force exerted on the patient's skin by the garment. For example, as shown in FIG. 17A, a graph 1700 illustrates a set of hysteresis curves for a particular garment. In some examples, each garment can include one or more adjustable fittings that are configured to alter the initial tightness of the garment. As such, the hysteresis curves as shown in FIG. 17A illustrate an average maximum force and an average minimum force for a particular garment as measured for a number of patient torso circumferences. More specifically, as shown in FIG. 17A, upper curve 1702 represents the exerted force for a tight fitting of the garment, and a lower curve 1704 represents the exerted force for a loose fitting of the garment. Additionally, the graph 1700 illustrates how the force exerted by the garment (as shown on the y-axis in pounds of force) changes based upon the circumference of the patient's torso (shown on the x-axis in inches). Generally, as the patient's torso is larger, the force exerted by the garment is higher.

In order to convert the force to pressure, the following equation can be used:

$$Pressure = (2\Pi * Force)/(G * W)$$

wherein force is equal to the given force at a particular circumference (e.g., as shown in FIG. 17A), G is the circumference of the body/torso, and W is the width of the garment in contact with the patient's skin. As such, the information as contained in FIG. 17A can be converted to a corresponding pressure graph. It should be noted that the above equation is provided by way of example only, and additional equations can be used to convert a measured force to a pressure.

Figure 17B:
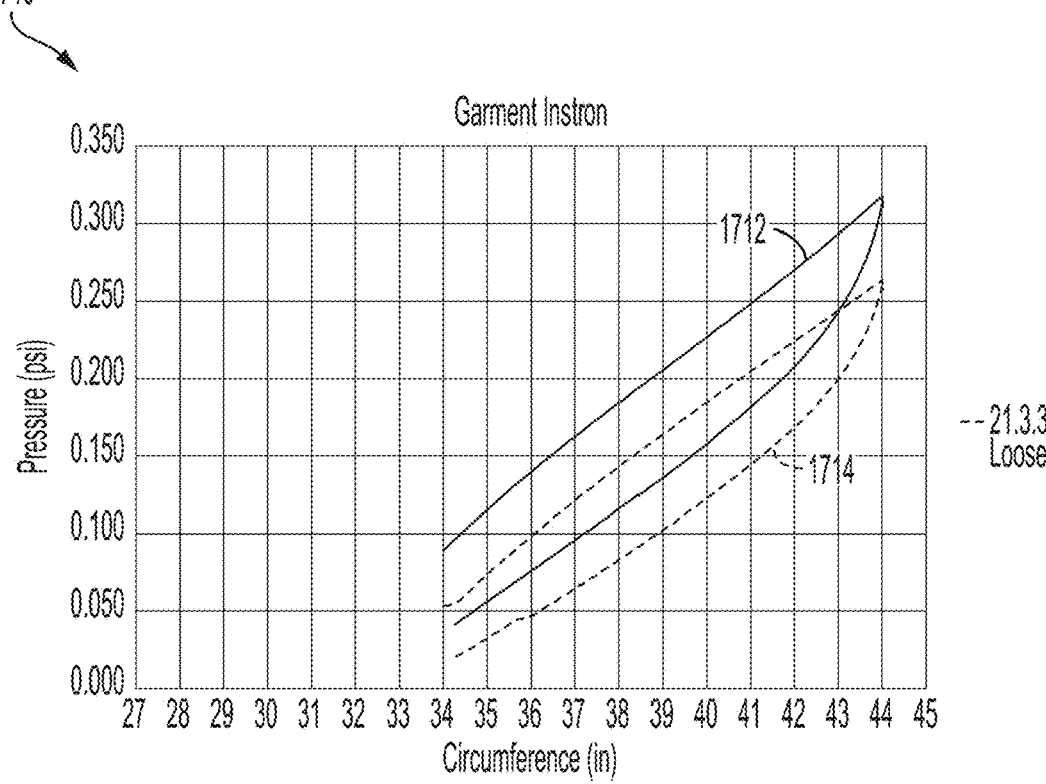

FIG. 17B illustrates graph 1710 illustrating a set of pressure hysteresis curves that correspond to the curves as shown in graph 1700 of FIG. 17A. For example, curve 1712 represents the exerted pressure of a tight fitting of a garment over a range of patient torso circumferences, and a curve 1714 represents the exerted pressure of a loose fitting of the garment over a range of patient torso circumferences. For example, as shown in graph 1710, curve 1712 shows that the garment exerts a pressure between about 0.05 psi and about 0.32 psi depending upon the patient's torso circumference when the garment is in the tight fitting and a pressure between about 0.025 psi and about 0.26 psi depending upon the patient's torso circumference when in the loose fitting. When performing an initial fitting and/or baselining as described herein, the caregiver performing the fitting can provide or otherwise input an indication of the garment being used to the medical device controller. The medical device controller can store the appropriate pressure curve information (e.g., curve 1712 as shown in FIG. 17B) for the garment. The caregiver can also input the patient's torso circumference. Based upon this information, the medical device controller can calculate the average pressures exerted on the patient's torso by the garment. The medical device controller can use this information to calibrate the pressure sensors and for applicators during the initial fitting as well, calibrating the initial settings of the components based upon the initial pressure characteristics of the garment. For example, when the force applicators are configured to exert no additional force on a corresponding physiological sensor, the medical device controller can be configured to determine that the output of a corresponding pressure sensor at that location is the exerted pressure as indicated by the related hysteresis curve associated with only the pressure being exerted by the garment. As such, the medical device controller can be configured to calibrate both the force applicators and associated pressure sensors at the initial fitting such that an exerted pressure in the comfortable pressure range of 0.05 psi to 0.65 psi as described herein is maintained during extended wear.

It should be noted that the information as shown in graphs 1700 and 1710 in FIGS. 17A and 17B is provided by way of example only. Depending upon a design of a garment (e.g., the shape, the size, combinations of materials used, etc.), the exerted pressure information as it corresponds to patient torso can vary accordingly.

Figure 18A:
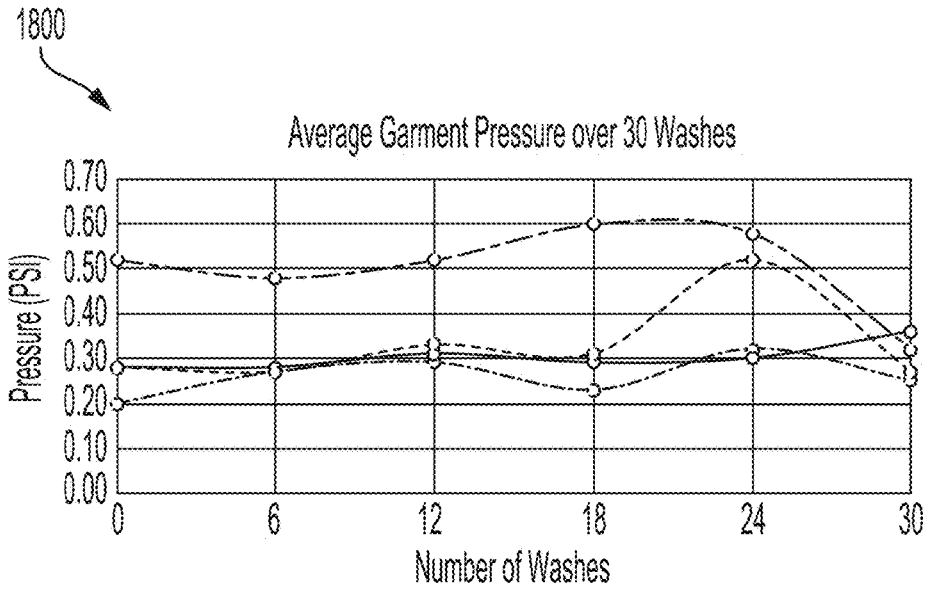
FIGS. 18A and 18B illustrate sample graphs depicting changes in exerted forces by a medical device garment over time, in accordance with an example of the present disclosure.

Additionally, over time, the exerted pressure as exerted by a garment can change over time. For example, as a garment is washed, the elasticity of one or more materials in the garment can change as a result of wear over time and the washing process and, as such, can impact the overall pressure as exerted by the garment. For example, as shown in FIG. 18A, the average pressure as exerted by a garment (as represented on the y-axis in psi) can change based upon the total time worn and the number of washes of the garment (as represented on the x-axis in number of washes). As shown in graph 1800, one garment (represented by the top line in the graph) shows that the average pressure of a sample garment changes from about 0.50 psi to about 0.30 psi over time. The systems and methods as described herein can be used to adjust the pressure exerted by, for example, one or more physiological sensors onto a corresponding anatomical location on the patient's body, thereby overcoming the inherent changes in exerted pressure by the garment over the lifetime of the garment.

Figure 18B:
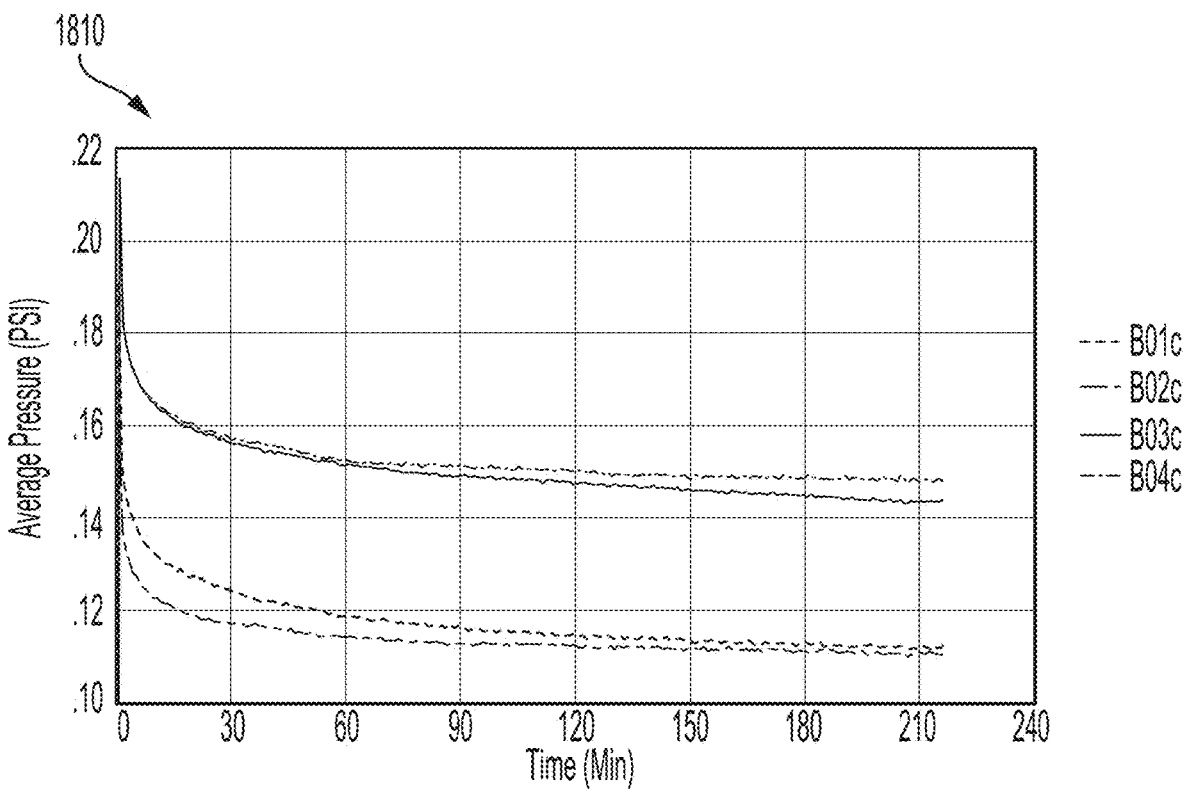

Similarly, the exerted pressure of a garment can change during a single wearing of the garment. For example, as a result of changes in the elasticity of the material of the garment, the pressure exerted by the garment when the garment is initially put on by the patient can be higher that the pressure exerted by the garment after the patient has worn the garment for a period of time. For example, as shown in FIG. 18B, graph 1810 illustrates changes in exerted pressure by a garment (as represented on the y-axis in psi) over time (as represented on the x-axis in minutes). As shown, the pressure exerted by a sample garment can decrease from about 0.21 psi to about 0.16 psi after being worn for about 30 minutes. The systems and methods as described herein can be used to adjust the pressure exerted by, for example, one or more physiological sensors onto a corresponding anatomical location on the patient's body, thereby overcoming the inherent changes in exerted pressure by the garment when being worn.

It should be noted that the information as shown in graphs 1800 and 1810 in FIGS. 18A and 18B is provided by way of example only. Depending upon a design of a garment (e.g., the shape, the size, combinations of materials used, etc.), the exerted pressure information and the associated changes in pressure information over time can vary accordingly.

Figure 12A:
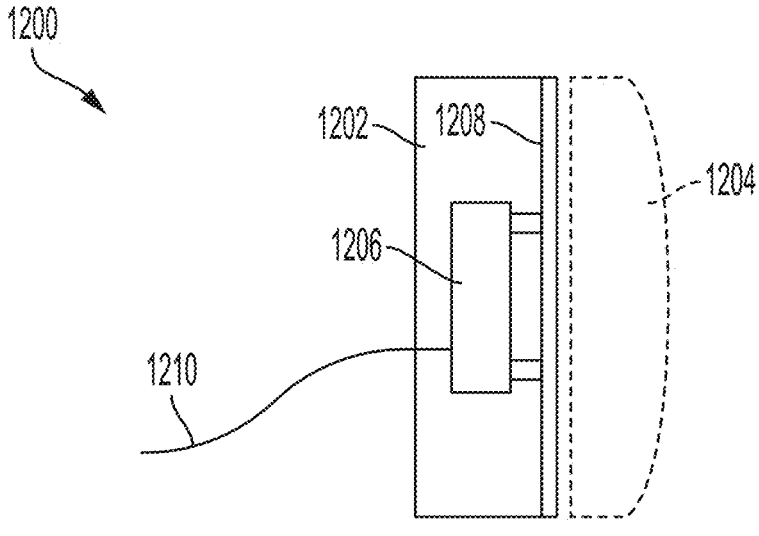
FIGS. 12A-12C illustrate examples of sample force applicators that are configured to automatically adjust their exerted pressure, in accordance with an example of the present disclosure.
Figure 12B:
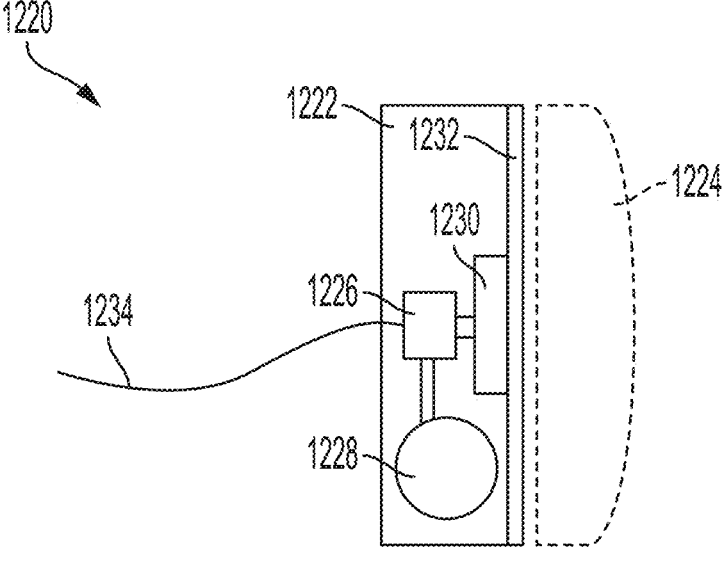
Figure 12C:
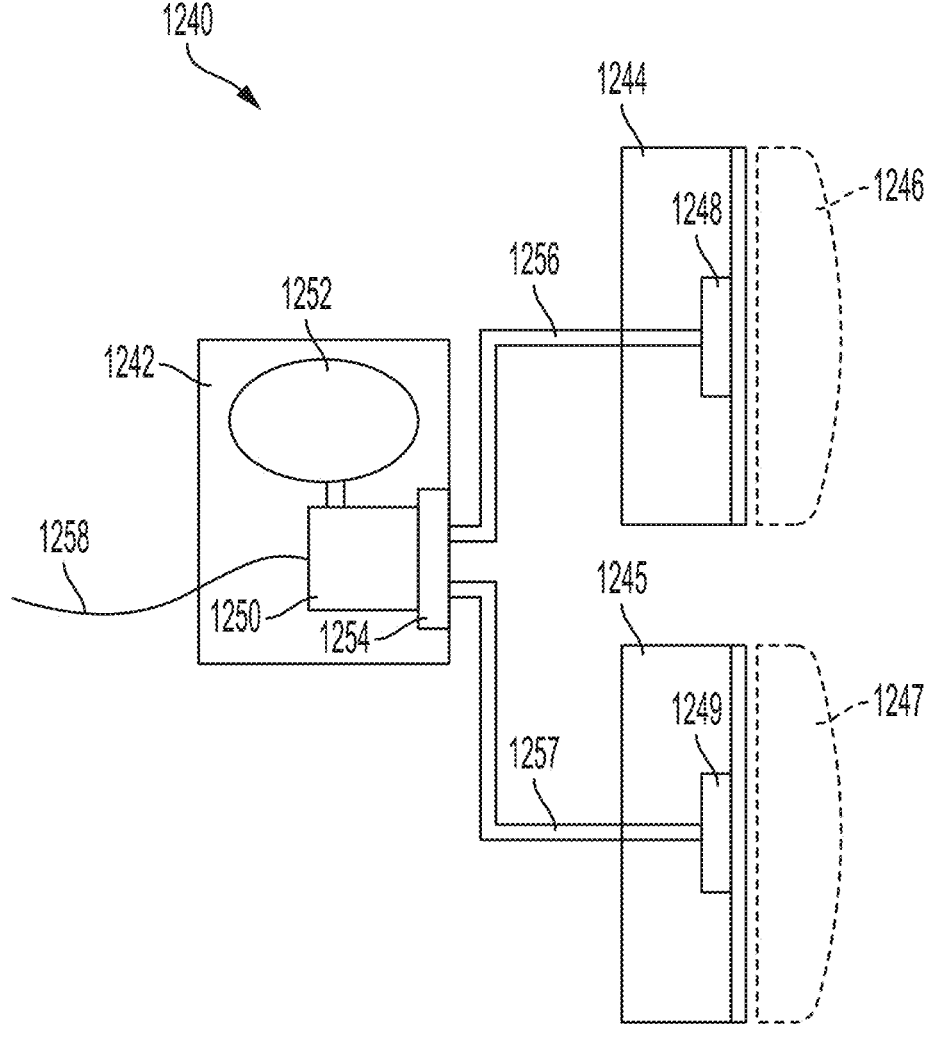

As noted herein, in certain implementations a force applicator can receive a force control signal and automatically adjust its output or exerted force in response to changes in the force control signal. Similarly, in some implementations, a force applicator can be configured to be manually adjusted to change the force exerted by the force applicator. FIGS. 12A-12C illustrate various examples of automatically adjustable force applicators as described herein. FIGS. 13A-13D illustrate various examples of manually adjustable force applicators as described herein.

More specifically, FIG. 12A illustrates a force applicator assembly 1200 that includes an electro-mechanical actuator configured to adjust the force exerted. As shown in FIG. 12A, the assembly 1200 includes a force applicator 1202, a physiological sensor 1204, an actuator 1206, a force exerting component 1208, and a control line 1210. In certain examples, the control line 1210 can be configured to transmit or otherwise deliver a force control signal from a controller such as the controller 700. In response to the force control signal, the actuator 1206 can be configured to adjust an exerted force being applied to the force exerting component 1208. In response to changes to the force being applied to the force exerting component 1208, the force being exerted on the physiological sensor 1204 by the force applicator 1202 can be increased or decreased accordingly.

It should be noted that the actuator 1206 is shown as a mechanically expanding actuator by way of example only. In some implementations, the actuator 1206 can include a rotational component that is configured to apply varying force on the force exerting component 1208 based upon the position of the rotational component.

In addition to electro-mechanical actuation, a force applicator can include a fluid-based force exertion mechanism. For example, as shown in FIG. 12B, a force applicator assembly 1220 can include a fluid-based force exertion mechanism. As shown in FIG. 12B, the assembly 1220 includes a force applicator 1222, a physiological sensor 1224, a fluid pump 1226, a fluid reservoir 1228, a force exertion reservoir 1230, a force exerting component 1232, and a control line 1234. In certain examples, the control line 1234 can be configured to transmit or otherwise deliver a force control signal from a controller such as the controller 700. In response to the force control signal, the fluid pump 1226 can be configured to pump fluid from the fluid reservoir 1228 to the force exertion reservoir 1230 to increase the pressure between the physiological sensor 1224 and the patient's skin or, conversely, to pump fluid from the force exertion reservoir to the fluid reservoir to decrease the pressure between the physiological sensor 1224 and the patient's skin. In some examples, the fluid can be a food-grade and safe liquid such as water, oil, or another similar non-toxic liquid. As such, by adjusting the amount of fluid in the force exertion reservoir 1230, the amount of force being exerted by the force exerting component 1232 on the physiological sensor 1224 can be adjusted.

In some examples, the fluid can include a gas such as air. The gas can be stored in the reservoir 1228 and pumped to the force exertion reservoir. As such, it should be noted that a pump and reservoir assembly such as that shown in FIG. 12B is provided by way of example only. In certain implementations, a fluid-based force exertion mechanism can include a gas pump or generator that is configured to pump gas into or out of, for example, an air bladder positioned adjacent to a force exerting component as described herein. By changing the volume and pressure of air within the bladder, the force exerted by the force exerting component can be adjusted.

As shown in FIG. 12B, such a fluid-based force exertion mechanism includes a localized fluid pump and reservoir assembly. However, as noted above, various force applicators and sensors can be arranged into groups or two or more force applicator and sensor assemblies. In such an example, a common pump and reservoir assembly can be used for multiple force applicators. Such an example is shown in FIG. 12C.

More specifically, as shown in FIG. 12C, a force exertion assembly 1240 can include a single pump and reservoir assembly 1242 that is configured to pump fluid to or pump fluid out of a local reservoir at multiple force applicators. For example, as shown in FIG. 12C, a force applicator 1244 can be positioned adjacent to a physiological sensor 1246 and include a local reservoir 1248. Similarly, a force applicator 1245 can be positioned adjacent to a physiological sensor 1247 and include a local reservoir 1249. The pump and reservoir assembly can include a fluid pump 1250, a fluid reservoir 1252, and a manifold 1254. The assembly 1242 can be fluidly connected to the force applicator 1244 via the tubing 1256. Similarly, the assembly 1242 can be fluidly connected to the force applicator 1245 via the tubing 1257. The assembly 1242 can also be connected to a controller such as the controller 700 via wire 1258. The pump 1250 can receive one or more control signals from the controller via the wire 1258. In response to the control signals, the pump can pump fluid to a local reservoir at the force applicator 1244 and/or the force applicator 1245. For example, if the control signal indicates that the force exerted by the force applicator 1244 is to be increased, the pump 1250 can pump fluid from the reservoir 1252 to the local reservoir 1248 via the manifold 1254 and the tubing 1256. Similarly, if the control signal indicates that the force exerted by the force applicator 1245 is to be reduced, the pump 125o can pump fluid from the local reservoir 1249 through the tubing 1257 and the manifold 1254, back into the reservoir 1252.

As such, the assembly 1240 as shown in FIG. 12C can provide for control over the exerted force of multiple force applicators using a single pump and reservoir assembly. However, it should be noted that two force applicators are shown in FIG. 12C by way of example only. In actual implementation, the number of force applicators fluidly connected to a single pump and reservoir assembly can be altered based upon the overall design and number of force applicators used.

As noted above, a force applicator can also be configured to allow for manual adjustment of the force being exerted by the force applicator. FIGS. 13A-13D illustrate various examples of manually adjustable force applicators.

Figure 13A:
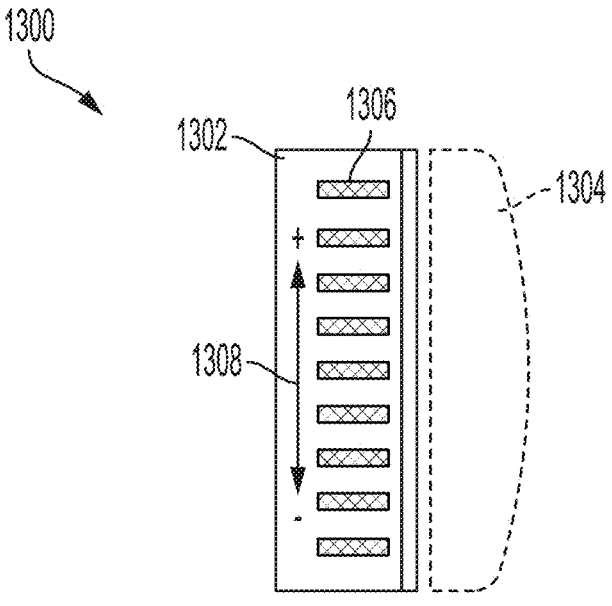
FIGS. 13A-13D illustrate examples of sample force applicators that are configured to manually adjust to alter their exerted pressure, in accordance with an example of the present disclosure.

For example, FIG. 13A illustrates a force applicator assembly 1300 that includes a toolless force adjustment mechanism. As shown in FIG. 13A, the assembly 1300 includes a force applicator 1302, a physiological sensor 1304, a mechanical adjustment interface 1306, and a visual indicator 1308. In this example, the mechanical adjustment interface 1306 is a series of notches or other similar controls that a user can physically grasp to manipulate a portion of the force applicator 1302 to, in this example, rotate about a central axis to adjust the force exerted by the force applicator 1302. The visual indicator 1308 provides a visual instruction for adjusting the force. For example, as shown in FIG. 13A, by rotating the mechanical adjustment interface 1306 upwards, one can increase the pressure exerted by the force applicator 1302 while rotating the mechanical adjustment interface downwards, one can decrease the pressure exerted by the force applicator 1302.

Figure 13B:
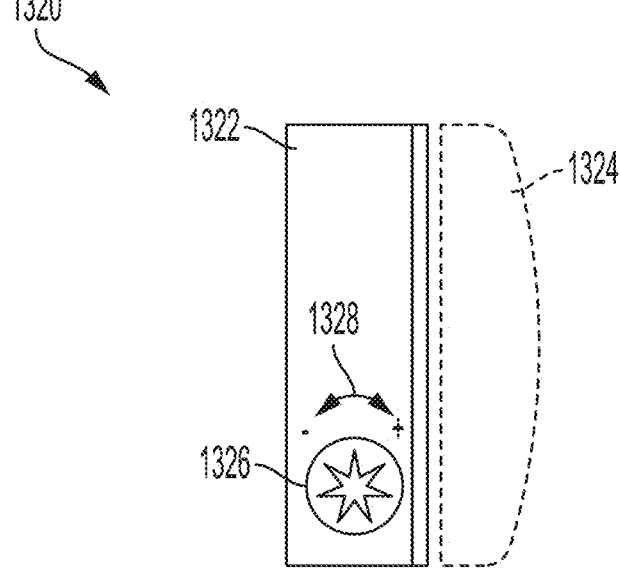

In another example, FIG. 13B illustrates a force applicator assembly 1320 that includes a tooled force adjustment mechanism. As shown in FIG. 13B, the assembly 1320 includes a force applicator 1322, a physiological sensor 1324, a tooled mechanical adjustment interface 1326, and a visual indicator 1328. In this example, the tooled mechanical adjustment interface 1326 is configured to receive a star-shaped tool that, upon turning in a clockwise or counterclockwise motion, is configured to manipulate a portion of the force applicator 1322 to, in this example, adjust the force exerted by the force applicator 1322. The visual indicator 1328 provides a visual instruction for adjusting the force. For example, as shown in FIG. 13B, by rotating the tooled mechanical adjustment interface 1326 clockwise, one can increase the pressure exerted by the force applicator 1322 while rotating the tooled mechanical adjustment interface counterclockwise, one can decrease the pressure exerted by the force applicator 1322.

Figure 13C:
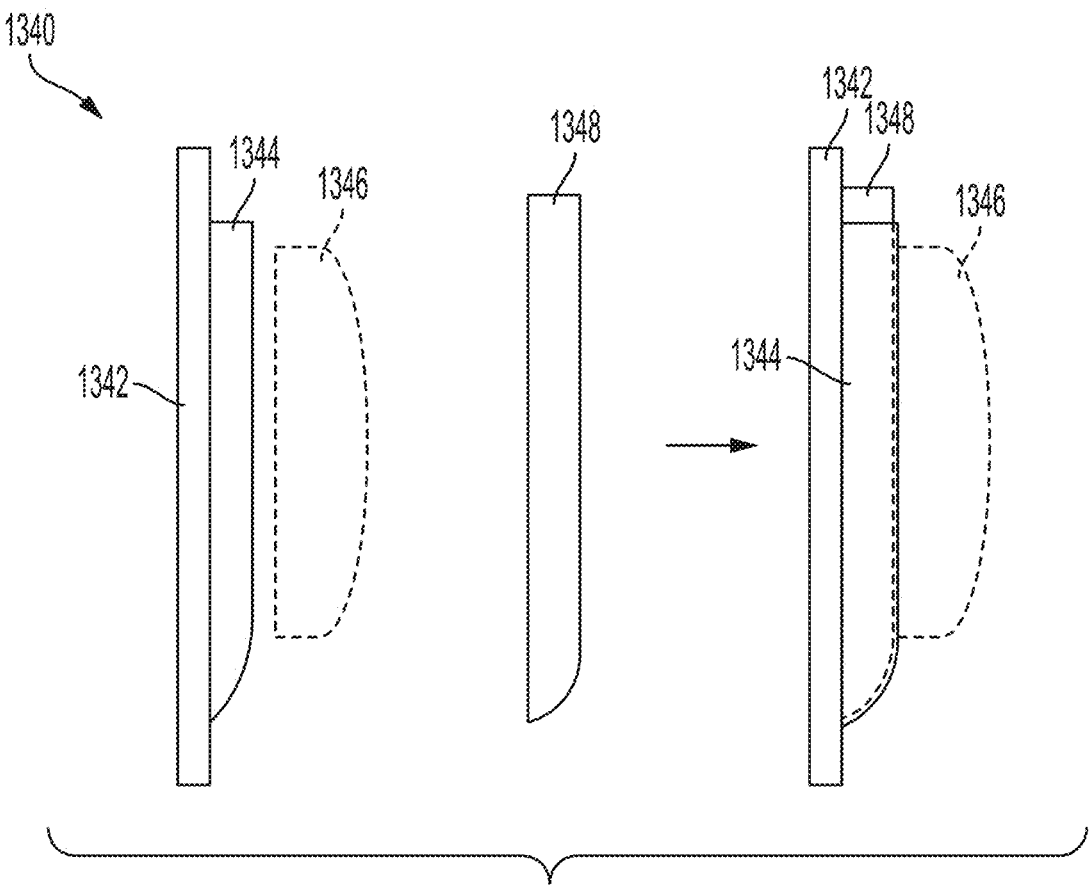

In another example, the force applicator can be an insertable component that is configured to be inserted between a portion of a garment and a physiological sensor to provide an exerted force on the physiological sensor. As shown in FIG. 13C, an assembly 1340 can include an insertable force applicator. More specifically, assembly 1340 includes a garment 1342, a pocket 1344 or other similar receptacle, a physiological sensor 1346, and a force applicator 1348. As shown on the left of the arrow in FIG. 13C, pocket 1344 is empty and there is a gap between the pocket 1344 and the physiological sensor 1346. As further shown on the right side of the arrow in FIG. 13C, when the force applicator 1348 is inserted into the pocket 1344, the pocket 1344 is expanded and contacts the physiological sensor 1346, thereby exerting a force on the physiological sensor 1346. As such, the force applicator 1348 acts as a shim or other similar wedge configured to fill the space between the garment 1342 and the physiological sensor 1346.

It should be noted that one force applicator 1348 is shown in FIG. 13C by way of example only. In certain implementations, additional force applicators 1348 can be inserted into the pocket 1344 to increase the force exerted onto the physiological sensor 1346. Similarly, one or more force applicators 1348 can be removed from pocket 1344 to reduce the force exerted on the physiological sensor 1346.

In certain implementations, a manually adjustable force applicator can include a gauge or other similar scale that provides a quick reference as to how much force is being exerted by a force applicator. For example, as shown in FIG. 13D, a force applicator can include a visual gauge that indicates exerted pressure.

Figure 13D:
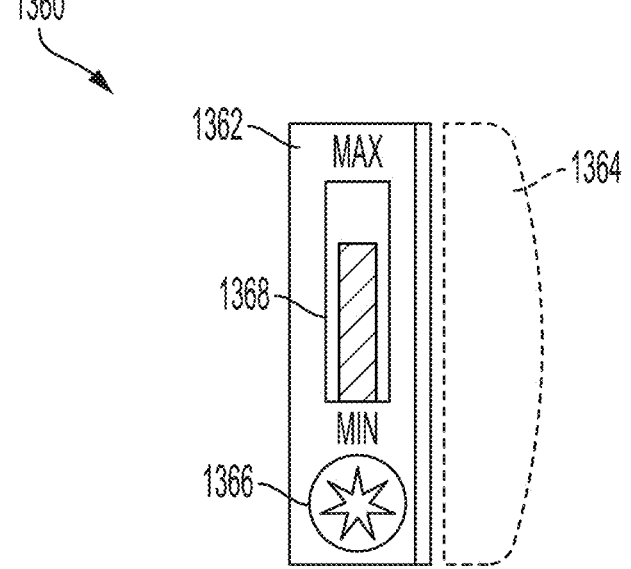

More specifically, assembly 1360 as shown in FIG. 13D includes a force applicator 1362, a physiological sensor 1364, a mechanical adjustment interface 1366, and a force gauge 1368. As the pressure exerted by the force applicator 1362 on the physiological sensor 1364 is increased as a result of manipulation of the mechanical adjustment interface 1366, the force gauge 1368 can change accordingly to illustrate what portion of total available force is being exerted by the force applicator. For example, if the mechanical adjustment interface 1366 is manipulated such that the force applicator 1362 is exerting a maximum potential force, the gauge 1368 can reflect that the force is at the maximum. Similarly, if the mechanical adjustment interface 1366 is manipulated such that the force applicator 1362 is exerting a minimum amount of potential force, the gauge 1368 can reflect that the force is at the minimum.

It should be noted that the type and position of the force gauge 1368 as shown in FIG. 13D is provided by way of example only. Depending upon the design and functionality of the force applicator, the type of gauge used, and the position of the gauge can vary accordingly. For example, if the force applicator is designed to receive power from, for example, a controller and includes a pressure sensor, the gauge can be configured as a visual display configured to output information related to the force being exerted by the force applicator as well as the pressure being measured by the pressure sensor.

The teachings of the present disclosure can be generally applied to external medical monitoring and/or treatment devices that include one or more sensors as described herein. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe). In such an example, nearly continuous can include 23.5 hours a day of wear with a half hour removal period.

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other non-ECG physiologic param-eters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include auto-mated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to moni-tor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 7 illustrates an example component-level view of a medical device controller 700 included in, for example, a wearable medical device. As further shown in FIG. 7, the therapy delivery circuitry 702 can be coupled to one or more electrodes 720 configured to provide therapy to the patient. For example, the therapy delivery circuitry 702 can include, or be operably connected to, circuitry compo-nents that are configured to generate and provide an elec-trical therapeutic shock. The circuitry components can include, for example, resistors, capacitors, relays and/or switches, electrical bridges such as an h-bridge (e.g., includ-ing a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 718) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capaci-tors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementa-tions, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as mono-phasic pulses). For example, an amplitude and a width of the two phases of the energy waveform can be automatically adjusted to deliver a precise energy amount (e.g., 150 joules) regardless of the patient's body impedance. The therapy delivery circuitry 702 can be configured to perform the switching and pulse delivery operations, e.g., under control of the processor 718. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

In certain examples, the therapy delivery circuitry 702 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 704 can include one or more of non-transitory computer-readable media, such as flash memory, solid state memory, magnetic memory, optical memory, cache memory, combinations thereof, and others. The data storage 704 can be configured to store executable instruc-tions and data used for operation of the medical device controller 700. In certain examples, the data storage can include executable instructions that, when executed, are configured to cause the processor 718 to perform one or more operations. In some examples, the data storage 704 can be configured to store information such as ECG data as received from, for example, the sensing electrode interface.

In some examples, the network interface 706 can facilitate the communication of information between the medical device controller 700 and one or more other devices or entities over a communications network. For example, where the medical device controller 700 is included in an ambulatory medical device, the network interface 706 can be configured to communicate with a remote computing device such as a remote server or other similar computing device. The network interface 706 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 700. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 708 can include one or more physical interface devices such as input devices, output devices, and combination input/output devices and a software stack configured to drive operation of the devices. These user interface elements can render visual, audio, and/or tactile content. Thus, the user interface 708 can receive input or provide output, thereby enabling a user to interact with the medical device controller 700. In certain implementations, the user interface 708 can be configured to provide user feedback of the exerted pressures at one or more sensor-skin interfaces as described herein, for example, in the discussion of process 110 as shown in FIG. 11.

The medical device controller 700 can also include at least one rechargeable battery 710 configured to provide power to one or more components integrated in the medical device controller 700. The rechargeable battery 710 can include a rechargeable multi-cell battery pack. In one example implementation, the rechargeable battery 710 can include three or more 2200 mAh lithium ion cells that provide electrical power to the other device components within the medical device controller 700. For example, the rechargeable battery 710 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 700.

The sensor interface 712 can include physiological signal circuitry that is coupled to one or more sensors configured to monitor one or more physiological parameters of the patient. As shown, the sensors can be coupled to the medical device controller 700 via a wired or wireless connection. The sensors can include one or more ECG sensing electrodes 722, and non-ECG physiological sensors 723 such as vibration sensor 724, tissue fluid monitors 726 (e.g., based on ultra-wide band RF devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 722 can be configured to monitor a patient's ECG information. For example, by design, the digital sensing electrodes 722 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 722 can be used with an electrolytic gel dispersed between the electrode surface and the patient's skin. In certain implementations, the electrodes 722 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 7, the vibration sensors 724 can be configured to detect cardiac or pulmonary vibration information. For example, the vibration sensors 724 can detect a patient's heart valve vibration information. For example, the vibration sensors 724 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 724 can also be configured to detect heart wall motion, for instance, by placement of the sensor in the region of the apical beat. The vibration sensors 724 can include a vibrational sensor configured to detect vibrations from a patient's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 724 can also include a multi-channel accelerometer, for example, a three-channel accelerometer configured to sense movement in each of three orthogonal axes such that patient movement/body position can be detected and correlated to detected cardio-vibrations information. The vibration sensors 724 can transmit information descriptive of the cardio-vibrations information to the sensor interface 712 for subsequent analysis.

The tissue fluid monitors 726 can use RF based techniques to assess fluid levels and accumulation in a patient's body tissue. For example, the tissue fluid monitors 726 can be configured to measure fluid content in the lungs, typically for diagnosis and follow-up of pulmonary edema or lung congestion in heart failure patients. The tissue fluid monitors 726 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 726 can transmit information descriptive of the tissue fluid levels to the sensor interface 712 for subsequent analysis.

As further shown in FIG. 7, the controller 700 can further include an accelerometer interface 730 and a set of accelerometers 732. The accelerometer interface 730 can be operably coupled to each of the accelerometers 732 and configured to receive one or more outputs from the accelerometers. The accelerometer interface 730 can be further configured to condition the output signals by, for example, converting analog accelerometer signals to digital signals (if using an analog accelerometer), filtering the output signals, combining the output signals into a combined directional signal (e.g., combining each x-axis signal into a composite x-axis signal, combining each y-axis signal into a composite y-axis signal, and combining each z-axis signal into a composite z-axis signal). In some examples, the accelerometer interface 730 can be configured to filter the signals using a high-pass or band-pass filter to isolate the acceleration of the patient due to movement from the component of the acceleration due to gravity.

Additionally, the accelerometer interface 730 can configure the output for further processing. For example, the accelerometer interface 730 can be configured to arrange the output of an individual accelerometer 732 as a vector expressing the acceleration components of the x-axis, the y-axis, and the z-axis as received from each accelerometer. The accelerometer interface 730 can be operably coupled to the processor 718 and configured to transfer the output signals from the accelerometers 732 to the processor for further processing and analysis.

As described above, one or more of the accelerometers 732 (e.g., accelerometers 108 as described above) can be integrated into one or more components of a medical device. For example, as shown in FIG. 7, an accelerometer 732 (e.g., accelerometer 108c as described above) can be integrated into the controller 700. In some examples, an accelerometer 732 can be integrated into one or more of a therapy electrode 720, a sensing electrode 722, a physiological sensor 723, and into other components of a medical device. When controller 700 is included in an HWD, an accelerometer can be integrated into an adhesive ECG sensing and/or therapy electrode patch.

In certain implementations, the cardiac event detector 716 can be configured to monitor a patient's ECG signal for an occurrence of a cardiac event such as an arrhythmia or other similar cardiac event. The cardiac event detector can be configured to operate in concert with the processor 718 to execute one or more methods that process received ECG signals from, for example, the sensing electrodes 722 and determine the likelihood that a patient is experiencing a cardiac event. The cardiac event detector 716 can be implemented using hardware or a combination of hardware and software. For instance, in some examples, cardiac event detector 716 can be implemented as a software component that is stored within the data storage 704 and executed by the processor 718. In this example, the instructions included in the cardiac event detector 716 can cause the processor 718 to perform one or more methods for analyzing a received ECG signal to determine whether an adverse cardiac event is occurring. In other examples, the cardiac event detector 716 can be an application-specific integrated circuit (ASIC) that is coupled to the processor 718 and configured to monitor ECG signals for adverse cardiac event occurrences. Thus, examples of the cardiac event detector 716 are not limited to a particular hardware or software implementation.

In some implementations, the processor 718 includes one or more processors (or one or more processor cores) that each are configured to perform a series of instructions that result in manipulated data and/or control the operation of the other components of the medical device controller 700. In some implementations, when executing a specific process (e.g., cardiac monitoring), the processor 718 can be configured to make specific logic-based determinations based on input data received and be further configured to provide one or more outputs that can be used to control or otherwise inform subsequent processing to be carried out by the processor 718 and/or other processors or circuitry with which processor 718 is communicatively coupled. Thus, the processor 718 reacts to specific input stimulus in a specific way and generates a corresponding output based on that input stimulus. In some example cases, the processor 718 can proceed through a sequence of logical transitions in which various internal register states and/or other bit cell states internal or external to the processor 718 can be set to logic high or logic low. As referred to herein, the processor 718 can be configured to execute a function where software is stored in a data store coupled to the processor 718, the software being configured to cause the processor 718 to proceed through a sequence of various logic decisions that result in the function being executed. The various components that are described herein as being executable by the processor 718 can be implemented in various forms of specialized hardware, software, or a combination thereof. For example, the processor 718 can be a digital signal processor (DSP) such as a 24-bit DSP. The processor 718 can be a multi-core processor, e.g., having two or more processing cores. The processor 718 can be an Advanced RISC Machine (ARM) processor such as a 32-bit ARM processor or a 64-bit ARM processor. The processor 718 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 718 of the controller 700 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 14A:
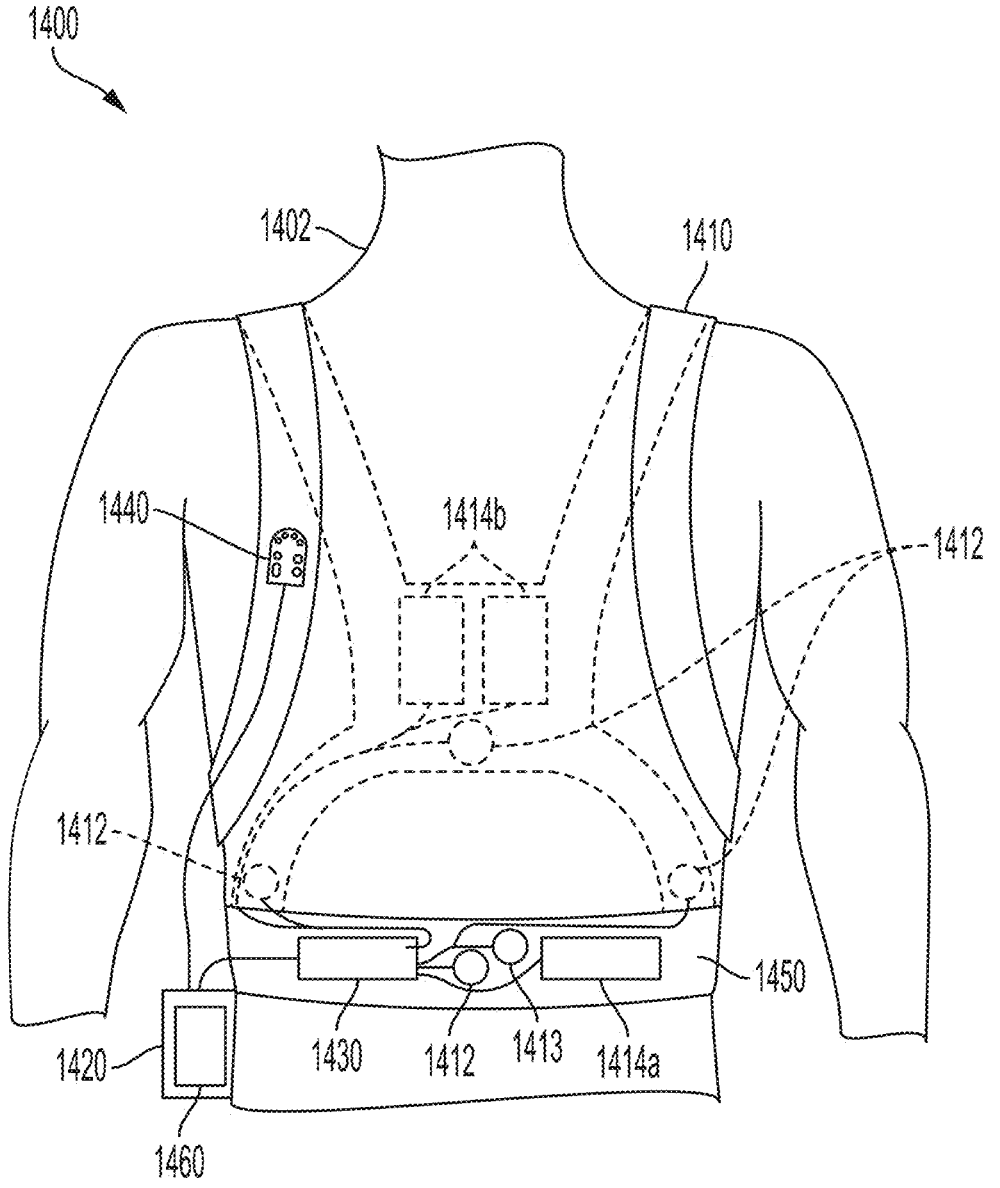
FIGS. 14A-14D illustrate sample ambulatory medical devices that may be prescribed to a heart failure patient, in accordance with an example of the present disclosure.

FIG. 14A illustrates an example medical device 1400 that is external, ambulatory, and wearable by a patient 1402, and configured to implement one or more configurations described herein. For example, the medical device 1400 can be a non-invasive medical device configured to be located substantially external to the patient. Such a medical device 1400 can be, for example, an ambulatory medical device that is capable of and designed for moving with the patient as the patient goes about his or her daily routine. For example, the medical device 1400 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1400 can include one or more of the following: a garment 1410, one or more ECG sensing electrodes 1412, one or more non-ECG physiological sensors 1413, one or more therapy electrodes 1414a and 1414b (collectively referred to herein as therapy electrodes 1414), a medical device controller 1420 (e.g., controller 700 as described above in the discussion of FIG. 7), a connection pod 1430, a patient interface pod 1440, a belt 1450, or any combination of these. In some examples, at least some of the components of the medical device 1400 can be configured to be affixed to the garment 1410 (or in some examples, permanently integrated into the garment 1410), which can be worn about the patient's torso.

The medical device controller 1420 can be operatively coupled to the sensing electrodes 1412, which can be affixed to the garment 1410, e.g., assembled into the garment 1410 or removably attached to the garment, e.g., using hook and loop fasteners. In some implementations, the sensing electrodes 1412 can be permanently integrated into the garment 1410. The medical device controller 1420 can be operatively coupled to the therapy electrodes 1414. For example, the therapy electrodes 1414 can also be assembled into the garment 1410, or, in some implementations, the therapy electrodes 1414 can be permanently integrated into the garment 1410. In an example, the medical device controller 1420 includes a patient user interface 1460 to allow a patient interface with the externally-worn device. For example, the patient can use the patient user interface 1460 to respond to activity related questions, prompts, and surveys as described herein.

Component configurations other than those shown in FIG. 14A are possible. For example, the sensing electrodes 1412 can be configured to be attached at various positions about the body of the patient 1402. The sensing electrodes 1412 can be operatively coupled to the medical device controller 1420 through the connection pod 1430. In some implementations, the sensing electrodes 1412 can be adhesively attached to the patient 1402. In some implementations, the sensing electrodes 1412 and at least one of the therapy electrodes 1414 can be included on a single integrated patch and adhesively applied to the patient's body.

The sensing electrodes 1412 can be configured to detect one or more cardiac signals. Examples of such signals include ECG signals and/or other sensed cardiac physiological signals from the patient. In certain examples, as described herein, the non-ECG physiological sensors 1413 such as accelerometers, vibrational sensors, RF-based sensors, and other measuring devices for recording additional non-ECG physiological parameters. For example, as described above, the such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1414 can also be configured to include sensors configured to detect ECG signals as well as other physiological signals of the patient. The connection pod 1430 can, in some examples, include a signal processor configured to amplify, filter, and digitize these cardiac signals prior to transmitting the cardiac signals to the medical device controller 1420. One or more of the therapy electrodes 1414 can be configured to deliver one or more therapeutic defibrillating shocks to the body of the patient 1402 when the medical device 1400 determines that such treatment is warranted based on the signals detected by the sensing electrodes 1412 and processed by the medical device controller 1420. Example therapy electrodes 1414 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1414 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 14B:
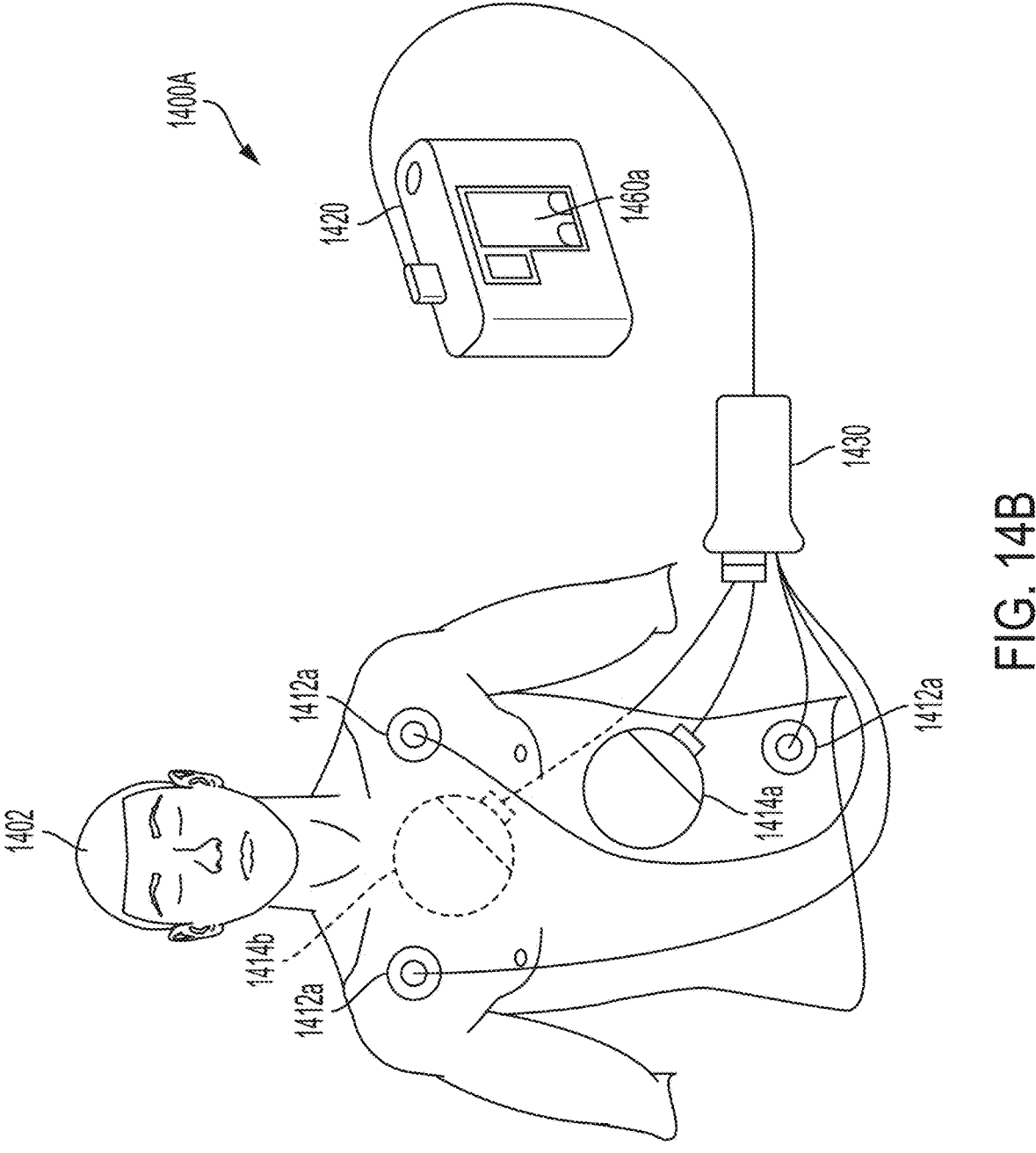

FIG. 14B illustrates a hospital wearable defibrillator 1400A that is external, ambulatory, and wearable by a patient 1402. Hospital wearable defibrillator 1400A can be configured in some implementations to provide pacing therapy, e.g., to treat bradycardia, tachycardia, and asystole conditions. The hospital wearable defibrillator 1400A can include one or more ECG sensing electrodes 1412a, one or more therapy electrodes 1414a and 1414b, a medical device controller 1420 and a connection pod 1430. For example, each of these components can be structured and function as like number components of the medical device 1400. For example, the electrodes 1412a, 1414a, 1414b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1414a attaches to the front of the patient's torso to deliver pacing or defibrillating therapy. Similarly, the back adhesively attachable therapy electrode 1414b attaches to the back of the patient's torso. In an example scenario, at least three ECG adhesively attachable sensing electrodes 1412a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1460a can be configured to interact with a user other than the patient, e.g., a nurse, for device-related functions such as initial device baselining, setting and adjusting patient parameters, and changing the device batteries.

In some examples, the hospital wearable defibrillator 1400A can further includes one or more motion sensors such as accelerometers. For example, an accelerometer can be integrated into one or more of a sensing electrode 1412*a* (e.g., integrated into the same patch as the sensing electrode), a therapy electrode 1414*a* (e.g., integrated into the same patch as the therapy electrode), the medical device controller 1420, the connection pod 1430, and various other components of the hospital wearable defibrillator 1400A.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 14A.

Figure 14C:
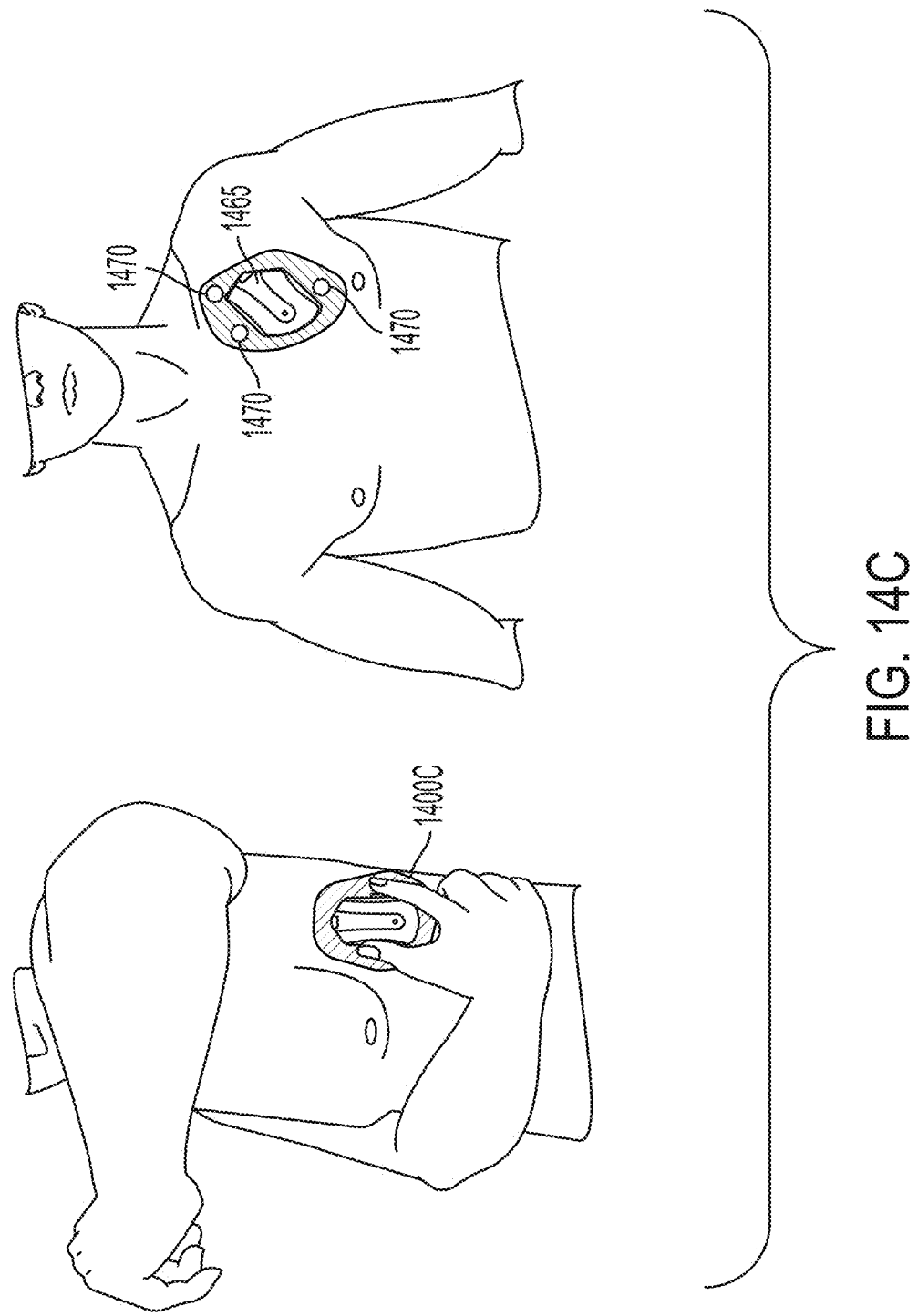
Figure 14D:
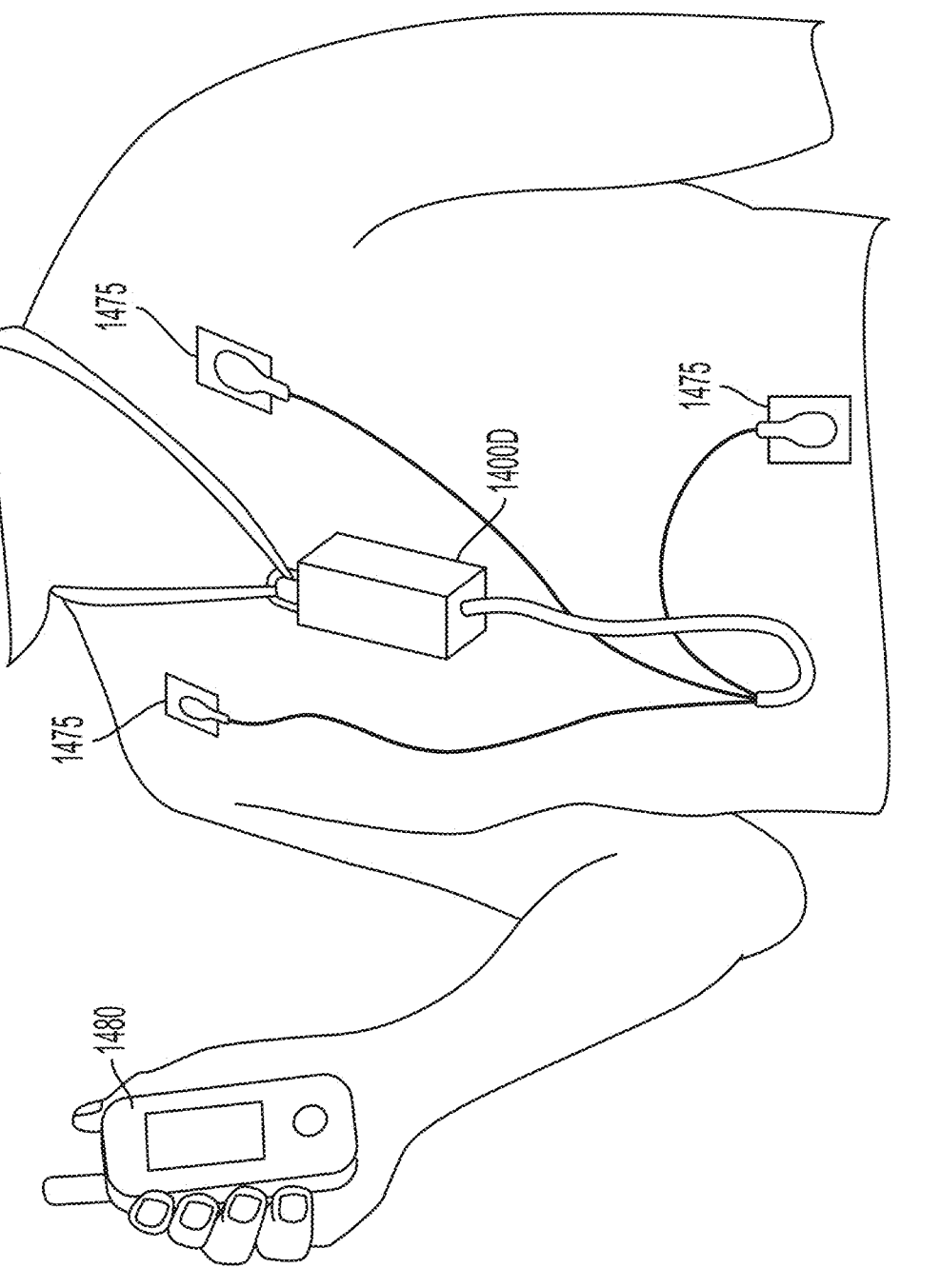

FIGS. 14C and 14D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 14C, an example wearable patient monitoring device 1400C can include tissue fluid monitors 1465 that use RF based techniques to assess fluid levels and accumulation in a patient's body tissue. Such tissue fluid monitors 1465 can be configured to measure fluid content in the lungs, typically for diagnosis and follow-up of pulmonary edema or lung congestion in heart failure patients. The tissue fluid monitors 1465 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1400C may be a cardiac monitoring device that also includes digital sensing electrodes 1470 for sensing ECG activity of the patient. Device 1400C can pre-process the ECG signals via one or more ECG processing and/or conditioning circuits such as an ADC, operational amplifiers, digital filters, signal amplifiers under control of a microprocessor. Device 1400C can transmit information descriptive of the ECG activity and/or tissue fluid levels via a network interface to a remote server for analysis. Additionally, in certain implementations, the device 1400C can include one or accelerometers for measuring motion signals as described herein.

Referring to FIG. 14D, another example wearable cardiac monitoring device 1400D can be attached to a patient via at least three adhesive digital cardiac sensing electrodes 1475 disposed about the patient's torso. Additionally, in certain implementations, the device 1400D can include one or accelerometers integrated into, for example, one or more of the digital sensing electrodes for measuring motion signals as described herein.

Cardiac devices 1400C and 1400D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 14A-14D) can communicate with a remote server via an intermediary or gateway device 1480 such as that shown in FIG. 14D. For instance, devices such as shown in FIGS. 14A-D can be configured to include a network interface communications capability as described herein in reference to, for example, FIG. 7.

Additionally, the devices described herein (e.g., FIGS. 14A-14D) can be configured to include one or more accelerometers as described herein. For example, as noted above in the discussion of FIGS. 3A and 3B, one or more sensors such as accelerometers, vibrational sensors, and RF sensors can be integrated into various components of a wearable device or included as standalone sensors configured to measure various signals for a patient.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable cardiac monitoring device for providing an improved fit to a body of a patient during long-term cardiac monitoring of the patient, the device comprising:

a garment configured to be worn about a torso of the patient and comprising a flexible material;

first and second electrocardiogram (ECG) sensors and associated circuitry configured to detect an ECG signal of the patient, the first ECG sensor disposed on the flexible material and positioned at a first anatomical location of the patient's torso and the second ECG sensor disposed on the flexible material and positioned at a second anatomical location of the patient's torso;

a first force applicator disposed on the flexible material proximate to the first ECG sensor, and a second force applicator disposed on the flexible material proximate to the second ECG sensor, each of the first and second force applicators configured to cause, during the long-term cardiac monitoring of the patient, a pressure to be exerted by the corresponding first and second ECG sensors onto the corresponding first and second anatomical locations of the patient's torso;

a first pressure sensor configured to measure a first pressure exerted by the first ECG sensor onto the first anatomical location of the patient's torso;

a second pressure sensor configured to measure a second pressure exerted by the second ECG sensor onto the second anatomical location of the patient's torso; and a controller configured to, in response to determining that at least one of the first or second pressures exerted by the corresponding first or second ECG sensors is outside of a pressure range, adjust the corresponding first or second force applicators to bring the first or second pressures exerted by the corresponding first or second ECG sensors back within the pressure range.

2. The device of claim 1, wherein the range is between 0.65 psi to 5.0 psi during an event.

3. The device of claim 2, wherein the range is between 0.05 psi and 0.65 psi after the event.

4. The device of claim 2, wherein the event comprises at least one of delivery of at least one treatment pulse, a radio-frequency (RF) monitoring period, a noise detection period and a monitoring period including a falloff event.

5. The device of claim 2, wherein the event spans a predetermined period of time.

6. The device of claim 5, wherein the predetermined period of time comprises at least one of 5 seconds, 10 seconds, 15 seconds, 20 seconds, 25 seconds, 30 seconds, 45 seconds, and 60 seconds.

7. The device of claim 1, wherein at least one force applicator of the first and second force applicators is configured to be calibrated to cause the pressure range to be exerted based on an external pressure measurement device.

8. The device of claim 7, wherein the external pressure measurement device comprises a pressure pad.

9. The device of claim 1, wherein the controller is configured to control the first and second force applicators during long term cardiac monitoring of the patient.

10. The device of claim 1, further comprising one or more therapy electrodes configured to deliver one or more therapeutic shocks to the patient.

11. The device of claim 10, wherein the one or more therapy electrodes are disposed between the first or second force applicators and the first or second anatomical locations such that the first or second force applicators are configured to cause the pressure to be exerted on the one or more therapy electrodes during delivery of the one or more therapeutic shocks to the patient.

12. The device of claim 1, further comprising an RF ultra-wide band transceiver circuit comprising one or more RF antennas and are configured to generate one or more RF-based measurements.

13. The device of claim 12, wherein the RF ultra-wide band transceiver circuit is configured to generate one or more RF-based measurements by being configured to:

control the one or more RF antennas to direct RF electromagnetic energy into a thoracic cavity of the patient; and derive RF information responsive to reflected RF electromagnetic energy received through the one or more RF antennas and reflected from within the thoracic cavity of the patient.

14. The device of claim 1, further comprising one or more vibrational sensors configured to detect one or more cardio-vibrational signals of the patient.

15. The device of claim 1, further comprising one or more sensor attachments disposed on the flexible material to receive and position the first or second ECG sensors at the first or second anatomical locations of the patient's torso.

16. The device of claim 15, wherein the one or more sensor attachments comprise one or more of a mechanical fastener, an enclosed receptacle, and an adhesive fastener.

17. The device of claim 15, wherein the first or second force applicator is configured to be removably coupled to at least one of the one or more sensor attachments and disposed within at least a portion of the garment corresponding to at least one of the one or more sensor attachments.

18. The device of claim 1, wherein the first and second force applicators comprise one or more electro-mechanical force applicators, one or more mechanical force applicators, or one or more fluid reservoir-based force applicators.

19. The device of claim 1, wherein the first and second force applicators are integrated into the first and second ECG sensors and associated circuitry.

20. The device of claim 1, wherein the first and second force applicators are integrated into the garment.

21. The device of claim 1, wherein the first and second pressure sensors are disposed on the flexible material proximate to the corresponding first and second force applicators.

22. The device of claim 1, wherein each of the first and second pressure sensors comprises at least one visual indicator configured to provide an indication of the pressure.

23. The device of claim 1, wherein the first and second pressure sensors are configured to operatively communicate with a remote computing device.

24. The device of claim 23, wherein the first and second pressure sensors are configured to transmit one or more pressure signals to the remote computing device.

25. The device of claim 1, wherein the wearable cardiac monitoring device is configured to be worn for a prescribed period of time during which the device provides the long-term cardiac monitoring of the patient, the prescribed period of time comprising at least one of at least three days, between three days and one week, between one week and two weeks, between two weeks and one month, between one month and three months, between three months and six months, and more than six months.

26. The device of claim 1, wherein the pressure range is between 0.05 psi and 0.65 psi.

27. The device of claim 1, wherein the pressure range is a user-specified pressure range.

* * * * *